(12) United States Patent
Harvey et al.

(10) Patent No.: US 8,785,702 B2
(45) Date of Patent: Jul. 22, 2014

(54) TURBINE AND DIESEL FUELS AND METHODS FOR MAKING THE SAME

(75) Inventors: Benjamin G. Harvey, Ridgecrest, CA (US); Roxanne L. Quintana, Ridgecrest, CA (US); Michael E. Wright, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 493 days.

(21) Appl. No.: 12/769,757

(22) Filed: Apr. 29, 2010

(65) Prior Publication Data

US 2012/0209036 A1 Aug. 16, 2012

Related U.S. Application Data

(63) Continuation-in-part of application No. 12/511,796, filed on Jul. 29, 2009, now Pat. No. 8,395,007, and a continuation-in-part of application No. 12/550,973, filed on Aug. 31, 2009, now Pat. No. 8,227,651.

(51) Int. Cl.
*C07C 2/14* (2006.01)
*C07C 5/03* (2006.01)

(52) U.S. Cl.
USPC .......... 585/255; 585/254; 585/510; 585/515; 585/520; 585/526

(58) Field of Classification Search
USPC .......... 585/14, 502, 510, 520, 310, 254, 255, 585/515, 526
See application file for complete search history.

(56) References Cited

U.S. PATENT DOCUMENTS

| | | | | |
|---|---|---|---|---|
| 2,181,640 A | * | 11/1939 | Deanesly et al. | 585/255 |
| 2,342,074 A | * | 2/1944 | Deanesly et al. | 585/16 |
| 3,179,711 A | * | 4/1965 | Antonsen | 585/524 |
| 4,234,752 A | | 11/1980 | Wu et al. | |
| 4,260,845 A | | 4/1981 | Shioyama | |
| 4,473,444 A | | 9/1984 | Feldman et al. | |
| 4,720,600 A | * | 1/1988 | Beech et al. | 585/330 |
| 4,772,736 A | | 9/1988 | Edwards et al. | |

(Continued)

FOREIGN PATENT DOCUMENTS

EP 173471 B1 6/1989
WO WO 2010/055935 A1 5/2010

(Continued)

OTHER PUBLICATIONS

Havery, et al., Synthesis of Renewable Jet and Diesel Fuels from 2-Ethyl-1-Hexene, journal "Energy and Environmental Science" on full disclosure Mar. 2010, in partNov. 13, 2009.

(Continued)

*Primary Examiner* — In Suk Bullock
*Assistant Examiner* — Bradley Etherton
(74) *Attorney, Agent, or Firm* — Charlene A. Haley

(57) ABSTRACT

A process for making diesel and turbine fuels including, providing an effective amount of branched olefins, adding active heterogeneous acid catalyst(s) to said branched olefins to produce a solvent-free mixture, heating said solvent-free mixture greater than about 100° C. for a desired amount of time depending on various conditions, to produce $C_{16}$ dimers/catalyst mixture, removing said catalysts from said dimers/catalyst mixture, and adding hydrogenation catalyst(s) to said dimers under hydrogen atmosphere to produce a mixture of stable fuels.

11 Claims, 11 Drawing Sheets

(56) References Cited

U.S. PATENT DOCUMENTS

| | | | |
|---|---|---|---|
| 5,158,992 A | 10/1992 | Casselli et al. | |
| 5,593,463 A * | 1/1997 | Gambini et al. | 44/300 |
| 5,625,106 A * | 4/1997 | Marks et al. | 585/512 |
| 5,830,821 A | 11/1998 | Rohrmann et al. | |
| 6,291,733 B1 | 9/2001 | Small et al. | |
| 6,500,999 B2 * | 12/2002 | Di Girolamo et al. | 585/510 |
| 6,518,473 B2 * | 2/2003 | Miller et al. | 585/517 |
| 6,548,723 B2 * | 4/2003 | Bagheri et al. | 585/517 |
| 6,929,705 B2 | 8/2005 | Myers et al. | |
| 7,271,304 B2 * | 9/2007 | Du Toit | 585/329 |
| 8,242,319 B1 | 8/2012 | Wright et al. | |
| 8,344,196 B2 | 1/2013 | Wright et al. | |
| 8,350,107 B2 | 1/2013 | Wright et al. | |
| 8,395,007 B2 | 3/2013 | Wright et al. | |
| 2001/0006154 A1 | 7/2001 | Krug et al. | |
| 2002/0177728 A1 | 11/2002 | Boudreaux et al. | |
| 2003/0125595 A1 | 7/2003 | Bagheri et al. | |
| 2005/0267271 A1 | 12/2005 | Mink et al. | |
| 2006/0194999 A1 * | 8/2006 | Brown et al. | 585/467 |
| 2006/0199984 A1 * | 9/2006 | Kuechler et al. | 585/1 |
| 2007/0185362 A1 | 8/2007 | Lattner et al. | |
| 2007/0293640 A1 | 12/2007 | Jiang et al. | |
| 2007/0293712 A1 | 12/2007 | Titta et al. | |
| 2008/0102502 A1 | 5/2008 | Foody et al. | |
| 2008/0132730 A1 | 6/2008 | Manzer et al. | |
| 2008/0216391 A1 | 9/2008 | Cortright et al. | |
| 2009/0124835 A1 | 5/2009 | Yamaguchi et al. | |
| 2009/0139134 A1 | 6/2009 | Yoshikuni et al. | |
| 2009/0299109 A1 | 12/2009 | Gruber et al. | |
| 2009/0305926 A1 | 12/2009 | Wu et al. | |
| 2010/0069589 A1 | 3/2010 | Bradin | |
| 2010/0155333 A1 | 6/2010 | Husain et al. | |
| 2010/0204925 A1 | 8/2010 | Albahri | |
| 2010/0330633 A1 | 12/2010 | Walther et al. | |
| 2011/0061290 A1 | 3/2011 | Aulich et al. | |
| 2011/0111475 A1 | 5/2011 | Kuhry et al. | |
| 2011/0114538 A1 | 5/2011 | Cosyns et al. | |
| 2011/0160502 A1 | 6/2011 | Wu et al. | |
| 2011/0172475 A1 | 7/2011 | Peters et al. | |
| 2012/0207648 A1 | 8/2012 | Wright et al. | |
| 2012/0209039 A1 | 8/2012 | Wright et al. | |
| 2012/0209040 A1 | 8/2012 | Wright et al. | |
| 2012/0209045 A1 | 8/2012 | Wright et al. | |
| 2012/0209047 A1 | 8/2012 | Wright et al. | |
| 2012/0238788 A1 | 9/2012 | Wright et al. | |
| 2013/0197279 A1 | 8/2013 | Wright et al. | |
| 2013/0253236 A1 | 9/2013 | Wright et al. | |

FOREIGN PATENT DOCUMENTS

| | | |
|---|---|---|
| WO | WO 2010/136289 A2 | 12/2010 |
| WO | PCT/US2012/035190 | 1/2013 |
| WO | WO2013032550 A8 | 5/2013 |

OTHER PUBLICATIONS

Williams, et al., "Kineticstudies of catalyticdehydration of tert-butanol on zeolite NaH-ZSM-5"; Journal of Catalysis [online], Jan. 1991, vol. 127, Iss. 1, pp. 377-392.

Leeuwen, et al., "New processes for the selective production of 1-octene"; Coordination Chemistry Reviews [online], Epub, Oct. 16, 2010, vol. 255, Iss. 13-14; pp. 1499-1517.

Wright, et al. Highly efficient zirconium-catalyzed batch conversion of 1-butene: A new route to Jet Fuel, Energy Fuels, Jul. 29, 2008, 22, (5) 3299-3302.

* cited by examiner

TURBINE AND DIESEL FUELS AND METHODS FOR MAKING THE SAME

CROSS-REFERENCE TO RELATED APPLICATIONS

This is a continuation-in-part and claiming the benefit of parent application Ser. No. 12/511,796 filed on Jul. 29, 2009, and this is a continuation-in-part and claiming benefit of parent U.S. Pat. No. 8,227,651, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to turbine and diesel fuels and methods for making the same, and more specifically, methods to convert renewable branched chain olefins including 2-ethyl-1-hexene to fuels suitable for use in turbine and diesel engines.

Figure 1:
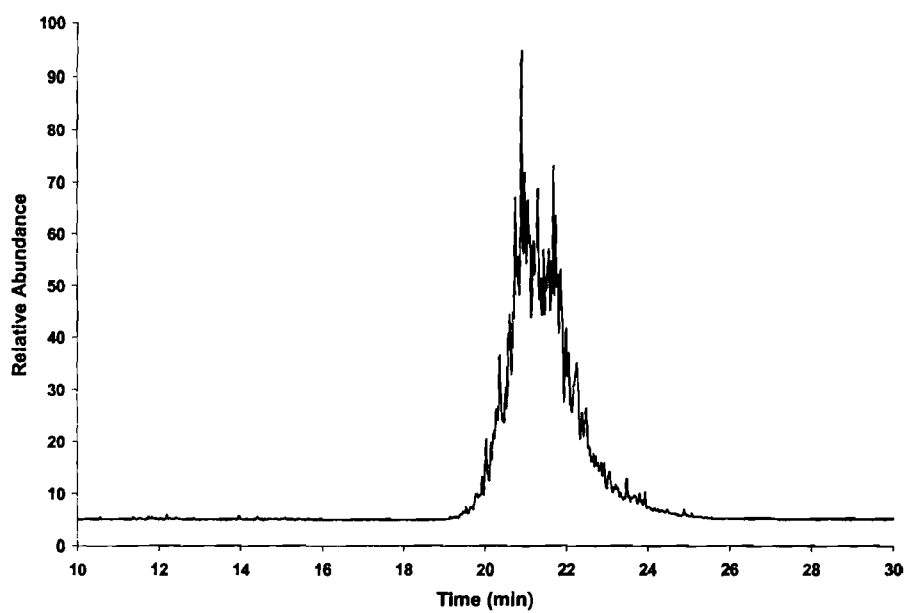
FIG. 1 is a GC/MS chromatogram of a dimerized β-pinene product mixture, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to turbine and diesel fuels and methods for making the same, and more specifically, methods to convert renewable branched chain olefins including 2-ethyl-1-hexene to fuels suitable for use in turbine and diesel engines.

Embodiments of the invention generally relate to a process for making fuels including providing an effective amount of branched olefins, adding active heterogeneous acid catalyst(s) to the branched olefins to produce a solvent-free mixture, heating the solvent-free mixture to greater than about 100° C. for a desired amount of time depending on various conditions to produce $C_{16}$ dimers/catalyst mixture, removing the catalysts from the dimers/catalyst mixture, and adding hydrogenation catalyst(s) to the dimers under a hydrogen atmosphere to produce a mixture of stable fuels. In embodiments, the step of providing branched olefins further includes a mixture of branched olefins. In embodiments, the step of adding active heterogeneous acid catalyst(s) to the branched olefins is performed under a $N_2$ atmosphere. In other embodiments, another step further includes the step of purifying the stable fuels by removing short chain branched olefins remaining in the stable fuels.

In embodiments, at least one branched olefin is 2-ethyl-1-hexene. In other embodiments, the heating step is performed under the temperatures ranging from about 110° C. to about 120° C. In other embodiments, the purifying step including filtration and/or distillation. In embodiments, the catalyst includes a Ziegler-Natta catalyst. In other embodiments, the catalyst further includes a co-catalyst. In embodiments, the fuels are claimed in accordance with the processes described herein. Furthermore, the butene oligomer fuels are claimed in accordance with the processes herein.

Another aspect of the invention generally relates to a process for making fuels including providing an effective amount of branched olefins including 2-ethyl-1-hexene, adding active heterogeneous acid catalyst(s) to the branched olefins to produce a solvent-free mixture, heating the solvent-free mixture greater than about 100° C. for a desired amount of time depending on various conditions to produce $C_{16}$ dimers/catalyst mixture, removing the catalysts from the dimers/catalyst mixture, and adding hydrogenation catalyst(s) to the dimers under hydrogen atmosphere to produce a mixture of stable fuels. In embodiments, the catalysts are selected from the group consisting of cation exchange resins, acid clays, zeolites, polyoxometallates, sulfated metal oxides, and other heterogeneous acids. In embodiments, the fuels are selected from the group consisting of 5,7-diethyl-5-methylundecane, 8-ethyl-5,6-dimethyldodecane, 6-ethyl-3-methyl-4-propyldecane, 5-ethyl-5,6,7-trimethylundecane, and 5-ethyl-3,5-dimethyl-4-propylnonane and similar molecules, or molecules produced from the coupling of any two structural isomers of 2-ethyl-1-hexene.

In related pending cases, high density fuel candidates have been synthesized in up to 90% yield from β-pinene, a renewable, strained, bicyclic compound derived from wood and plant sources. These novel syntheses are based on heterogeneous acidic catalysts (also referred to as heteropolyacidic catalysts) including Montmorillonite-K10 and Nafion® NR-50 which promote selective isomerization and dimerization of pinenes under moderate conditions (100° C., atmospheric pressure). Montmorillonite clays have been used as catalysts for a number of organic reactions and offer several advantages over classical acids. For example, they are highly acidic, non-corrosive, can be utilized under mild reaction conditions, and typically result in high yields with good selectivity. Additionally they are low cost, simple to use, and can be conveniently separated from reaction mixtures by decantation or filtration. Mesoporous Montmorillonite clays, which are dioctahedral phyllosilicates, are composed of hydrated sodium, calcium, aluminum, magnesium, silicate hydroxide $(Na,Ca)_{0.33}(Al,Mg)_2(Si_4O_{10})(OH)_2 \cdot nH_2O$, with an octahedral layer ($AlO_6$ units) sandwiched between two tetrahedral layers ($SiO_4$ units). Potassium, iron, and other cations are common impurities. These clays typically have a surface area of 220-270 $m^2/g$. Montmorillonite-K10 is a strong Bronsted and Lewis acidic catalyst shown to be highly active for the dimerization of β-pinene concomittant with ring opening followed by dehydrogenation to produce p-cymene. Use of this catalyst resulted in a dimer yield of dimer to about 75%. Nafion® NR-50 was capable of producing dimers in up to 90% yield but was less active than the acidic clay. Amberlyst-15, a common industrial catalyst had very poor activity and conversion even at 150° C.

The dimer mixtures were upgraded through hydrogenation over $PtO_2$ and fractional distillation. The synthesized fuels have a density of about 0.94 g/cc, and a net volumetric heating value of about 39.5 MJ/L (~141,745 BTU/gal). These values are nearly identical to those of the widely used tactical fuel JP-10 (which is primarily composed of exo-tetrahydrodicyclopentadiene), suggesting that these renewable fuels may have applications for rocket propulsion.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments which are illustrated schematically in the accompanying drawings and in the appended claims.

β-Pinene Dimerization

Note of caution: the dimerization reaction is very exothermic, particularly when MMT-K10 is used as the catalyst. Runaway reactions can occur with both MMT-K10 and Nafion, especially with concentrated solutions or in the absence of a suitable heat sink. Slow addition of β-pinene to a refluxing reaction mixture at 100° C. was determined to be the safest method of addition. In a typical procedure, the solid acid catalyst (100 mg Nafion or 500 mg MMT-K10) was slurried in 10 mL of n-heptane under a nitrogen atmosphere and heated to reflux. β-pinene (35 g) was then added dropwise to the slurry and the reflux was maintained with external heat for the remainder of the reaction; additional reactions were conducted over a range of temperatures from 0° C. up to the reflux temperature of β-pinene. Dimer mixtures were hydrogenated with 1 wt % $PtO_2$ under 1-2 psig of hydrogen for a period ranging from about 12 hours to about 24 hours. Subsequent distillations were carried out under reduced pressure (4 mm Hg).

Nafion® NR-50 (Aldrich) was precipitated from a 5% water/alcohol dispersion by addition of dichloromethane ($CH_2Cl_2$) and ether, followed by filtration and drying under vacuum (4 Torr) at ambient temperature (adapted from Kim, T. K.; Kang, M.; Choi, Y. S.; Kim, H. K.; Lee, W.; Chang, H.; Seung, D. *J. Power Sources* 2007 165, 1-8). The MMT-K10 (Aldrich) and dry Amberlyst-15 (Aldrich) were used directly from the bottle. (1S)-(−)-β-pinene (Aldrich) typically was used without further purification, or after an extended storage time, it was distilled from $CaH_2$ under a nitrogen atmosphere. Product mixtures were analyzed with an Agilent 6890-GC/5973-MS (gas chromatography mass spectrometer) to determine chemical compositions. The density of the product mixtures was measured with an Anton Parr DMA-35N density meter. Heat of combustion and elemental analyses were conducted under standard protocols by Southwest Research Institute.

α- and β-pinene have net heats of combustion of 132,300 and 132,500 BTU/gal respectively as calculated based on the experimental heat of formation as reported on http://webbook.nist.gov and by others (Hawkins, J. E.; Eriksen, W. T. J. Am. Chem. Soc. 1954 76, 2669 and Cox, J. D.; Pilcher, G. *Thermochemistry of Organic and Organometallic Compounds* Academic Press, New York 1970). In comparison, the net heat of combustion of JP-10 is 142,000 BTU/gal (Table 2) (Burdette, G. W.; Lander, H. R.; McCoy, J. R. *J. Energy* 1978, 2, 289-292). It should be noted that both pinene molecules also have positive gas phase heats of formation due to strain energy. A path to improving the volumetric heating value of these natural products is selective dimerization that would both increase the density and maintain the ring strain of these molecules. Two target dimer molecules are shown in Diagram 1. Semi-empirical calculations for both of these molecules give positive gas phase heats of formation and impressive values for net heat of combustion (based on a density of 0.94 g/mL); 146,900 BTU/gal and 146,500 BTU/gal for the hypothetical hydrogenated α- and β-pinene dimers, respectively. The gas phase data was calculated utilizing MOPAC, while a liquid phase net heat of combustion was calculated assuming a density of 0.94 g/mL and utilizing double the value of the heat of vaporization of β-pinene according to Hawkins and Armstrong (Hawkins, J. E.; Armstrong, G. T. *J. Am. Chem. Soc.* 1954 76, 3756). These calculations clearly suggest that dimerized pinenes have the potential to have heating values exceeding that of JP-10.

TABLE 1

Catalysts for the Dimerization of β-pinene.

| Catalyst | Temperature | Time | Products |
|---|---|---|---|
| MMT-K10 | 0-30° C. | 4 h | isomers |
| MMT-K10 | 100° C. | 1 h | dimer/isomers |
| MMT-K10 | 150° C. | 1 h | dimer/trimer/isomers |
| Amberlyst-15 | ambient | 24 h | NR |
| Amberlyst-15 | 150° C. | 3 h | isomers |
| Nafion | ambient | 24 h | NR |
| Nafion | 100° C. | 6 h | dimer/isomers |
| Nafion | 150° C. | 2 h | dimer/isomers/trimer |
| H2SO4 (98%) | 0° C. | 10 min | polymer |
| H2SO4 (50%) | 0° C. | 10 min | polymer |

TABLE 2

Selected properties of JP-10 and α- and β-pinene

|  | β-pinene | α-pinene | JP-10 |
|---|---|---|---|
| Density | 0.859 | 0.858 | 0.94 |
| ΔHf(g) (kJ/mole) | 35.8 | 30.2 | −96.6a |
| ΔHf(l) (kJ/mole) | −7.66 | −16.4 | −133.8b |
| ΔHc (BTU/gal)c | 132,500d | 132,300d | 142,000 | asemi-empirical calculation (MOPAC AlM1).

bcalculated from the experimental heat of combustion.

cnet heat of combustion.

dcalculated from the experimental heat of formation.

Diagram 1.
Structures of target
dimer molecules and selected calculated properties.

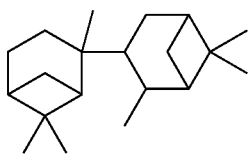

Hydrogenated α-pinene dimer

Calculated $\Delta H_f(g)$ = 48.6 kJ/mol
Calculated $\Delta H_f(l)$ = -44.6 kJ/mol
Calculated $\Delta H_c$(net) = 146,900 BTU/gal

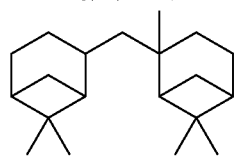

Hydrogenated β-pinene dimer

Calculated $\Delta H_f(g)$ = 4.2 kJ/mol
Calculated $\Delta H_f(l)$ = -82.7 kJ/mol
Calculated $\Delta H_c$(net) = 146,500 BTU/gal Montmorillonite K10

Initially MMT-K10 was targeted as a catalyst due to its low cost, abundance, and well established reactivity (Madhavan, D.; Murugalakshmi, M.; Lalitha, A.; Pitchumani, K. *Catalysis Letters* 2001 73, 1). MMT-K10 is a layered aluminosilicate functionalized with additional acidic sites through treatment with sulfuric acid. Its acidity can vary several orders of magnitude based on the amount of water present in the sample and it has both Lewis and Bronsted acidic sites (Pillai, S. M.; Ravindranathan, M. *J. Chem. Soc. Chem. Commun.* 1994 1813-1814). The clay can delaminate or separate into particles as little as 1 nm in width and several hundred nanometers in length. Upon addition of MMT-K10 to a flask containing β-pinene at room temperature, a vigorous reaction occurs, with the catalyst immediately turning red accompanied by a rapid exotherm. Without a heat sink, the reaction rapidly reaches the boiling point of β-pinene. In an effort to more effectively control the reaction, slow addition of β-pinene to a slurry of the catalyst in heptane at 0° C. under an inert atmosphere resulted in only a trace amount of isomers (detected by NMR) and no dimers, suggesting that the isomerization reaction is very slow at that temperature. Removal of the ice bath led to an exotherm that was controlled by sequentially submerging the rapidly stirred flask in an ice bath and then removing the flask and allowing the internal temperature to warm up to 30 (+/−5)° C. This was repeated several times until the temperature was stable at ambient temperature. At this point the reaction was monitored by both NMR and GC/MS revealing that the principal reaction was isomerization to a mixture of camphene, limonene and α-pinene, with some β-pinene remaining (Scheme 1). Small amounts of dimer, α- and γ-terpinene, and p-cymene were also observed, as well as a trace of oxidation products. The relative ratio of α-pinene:camphene:β-pinene:limonene was 3:5:2:4. Heating the mixture to the reflux temperature of heptane led to a vigorous reaction with production of significant amounts of hydrogen. After 1 h the overall yield of dimer molecules was 80% by GC/MS, with the balance of the product represented by primarily p-cymene, camphene, and tricyclene. Extended heating times at the reflux temperature of heptane did not change the concentration of camphene in the reaction mixture, suggesting that MMT-K10 is a poor catalyst for camphene dimerization. Although camphene represents 35% of the initial isomerized product, it represents only about 10% of the final product mixture.

Scheme 1. Mechanism for the isomerization of β-pinene over MMT-K10.

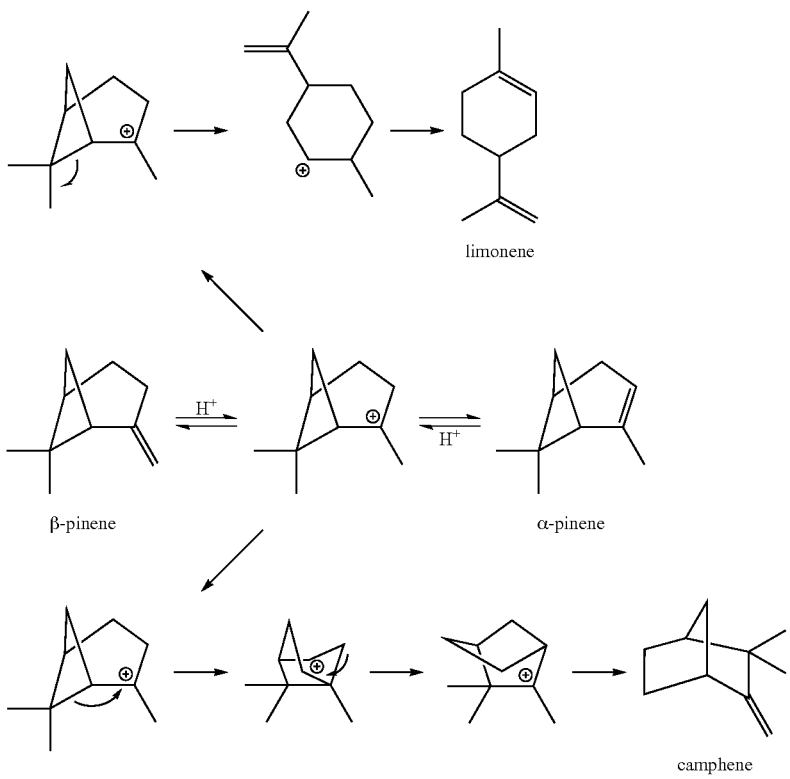

This suggests that although MMT-K10 is inefficient for the dimerization of camphene, it does promote the cross coupling of camphene with other isomers in solution. Another important product is p-cymene which is derived from limonene. Previous studies suggest that the mechanism for formation of p-cymene proceeds through a rearrangement/disproportionation reaction in which limonene rearranges to terpinenes which then disproportionate to p-cymene and a menthenes such as p-1-menthene (Scheme 2) (Fernandes, C.; Catrinescu, C.; Castilho, P.; Russo, P. A.; Carrott, M. R.; Breen, C. *Applied Catalysis A* 2007 318, 108-120). However, we observed that copious production of hydrogen was evident at the reflux temperature of heptane. This supports a direct dehydrogenative mechanism (Scheme 3) that could be catalyzed by the clay or possibly by polyaromatic coke deposits on the catalyst surface (Arnano, H.; Sato, S.; Takahashi, R.; Sodesawa, T. *Phys. Chem. Chem. Phys.* 2001 3, 873-879).

Scheme 2.
Potential mechanism for the conversion of β-pinene to p-cymene.

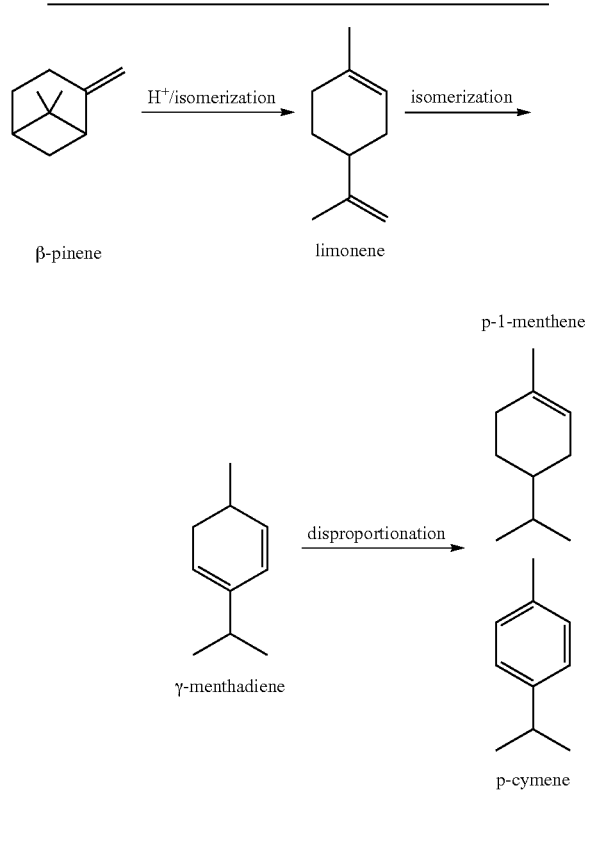

Scheme 3.
Potential mechanism for the conversion of β-pinene to p-cymene.

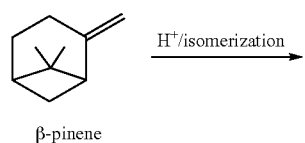

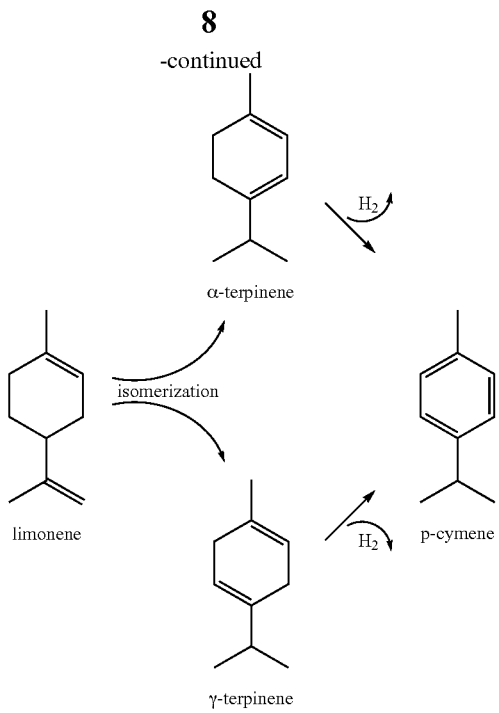

To shed some light on the mechanism, (R)-(+)-limonene was added dropwise to a stirred slimy of MMT in refluxing heptane. After one hour an NMR spectrum was collected and it was observed that limonene, p-cymene, α- and γ-terpinene and terpinolene were the primary low molecular weight components present. This result supports the second mechanism (Scheme 3), given that no evidence was observed for any menthene products. It is also of interest that the intermediate terpinolene was observed in the reaction mixture, suggesting that the isomerization reaction progresses in a step-like fashion (Scheme 4).

Scheme 4.
Stepwise conversion of limonene to terpinenes through terpinolene.

Although no menthene products were observed in the NMR spectrum, GC/MS analysis of an MMT limonene mixture in heptanes that had been refluxed overnight revealed the presence of p-cymene and residual menthenes, primarily p-menth-3-ene and p-menth-1-ene. The presence of these particular menthenes was expected based on the carbocationic mechanism of isomerization and the stability of intermediates with tertiary cationic centers. The data suggest that a competition exists between the first and second mechanism, with some disproportionation occurring through a dehydrogenative/hydrogenative mechanism and some direct loss of hydrogen ostensibly due to the slower rate of hydrogenation under these conditions. Additionally, many other potential reactants in solution including dimer molecules could react with the released hydrogen. The GC/MS analysis reveals that the dimer region is a complex mixture of peaks mainly with molecular weights of 272, while some peaks have m/z=274. It is unclear whether the molecule(s) represented by the m/z=274 peaks are produced by hydrogenation after dimerization of two monomers, or if they are produced from the coupling of a monoolefin and a diolefin. A recent report has suggested that under somewhat harsher conditions (150° C., acidic clay catalyst), terpinenes and other olefins undergo a Diels Alder reaction (Scheme 5) that is promoted by the Lewis acidity of the catalyst (Fernandes, C.; Catrinescu, C.; Castilho, P.; Russo, P. A.; Carrott, M. R.; Breen, C. *Applied Catalysis A* 2007 318, 108-120).

Scheme 5.
Example of a potential Diels Alder dimerization reaction of α-terpinene.

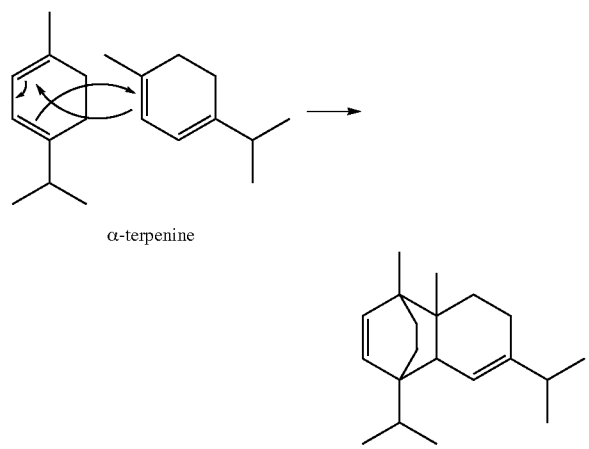

α-terpenine

Similar reactions could occur between terpenines and a variety of olefins in solution. Although the conversion to p-cymene is of interest, it limits the conversion of β-pinene to dimer products. In an attempt to efficiently control the heat of reaction and to selectively produce dimers incorporating ring strained cyclobutanes, β-pinene was added dropwise to a stirred slurry of MMT-K10 in refluxing heptane under a nitrogen atmosphere. Upon addition of the first drop the slurry turned green and then rapidly converted to a red/brown suspension. After the addition, the mixture was refluxed for an additional hour. Interestingly, the NMR spectra and GC-MS chromatograms were indistinguishable from those obtained when β-pinene was added slowly at room temperature and then heated to refluxing heptane temperatures. This result suggests that the rate of isomerization at the elevated temperature is faster than the rate of dimerization of β-pinene. To determine the effect of even higher temperatures, β-pinene was added neat to the clay catalyst in an open flask maintaining a slow flow of nitrogen. The mixture was vigorously stirred and rapidly rose in temperature until vigorous gas evolution was evident. After the bubbling had mostly subsided, the flask was placed in an oil bath at 150° C. and further evolved gas was allowed to slowly escape through a bubbler. The distribution of products was similar to that observed at 100° C. with the addition of about 10% trimer, leading to a 70/10/20 ratio for dimer/trimer/low molecular weight products. This result suggests that the intermediate temperature is ideal, leading to a high conversion to dimer while limiting the formation of trimer or other heavier oligomers. The clay catalyst can be removed with some difficulty from the reaction mixture by filtration, however as the catalyst is remarkably well dispersed it was often more convenient to separate the clay by centrifugation followed by decantation.

Amberlyst-15

Although MMT-K10 was found to be an efficient dimerization catalyst, in an attempt to produce a dimer mixture with less isomerized products and more molecules maintaining strained ring systems, Amberlyst-15, a sulfonic acid functionalized cross-linked polystyrene resin was investigated to determine its catalytic activity for the dimerization of β-pinene. Unlike MMT-K10, upon addition of neat β-pinene to beads of Amberlyst-15 under nitrogen, no reaction at room temperature occurred even upon reaction times of 48 hours. This difference in activity may be due to the presence of Lewis acidic sites present in MMT-K10 which may allow for coordination and isomerization of β-pinene at low temperature (Fernandes, C.; Catrinescu, C.; Castilho, P.; Russo, P. A.; Carrott, M. R.; Breen, C. *Applied Catalysis A* 2007 318, 108-120). Upon heating to 140° C. for 3 h, a mixture of primarily β-pinene and camphene were present with traces of p-cymene and dimer. Given the slow reaction rate, negligible conversion to dimer and high reaction temperature, Amberlyst-15 was not studied in further detail.

Nafion®

Nafion® is a sulfonated tetrafluoroethylene based fluoropolymer-copolymer incorporating perfluorovinyl ether groups terminated with sulfonate groups onto a tetrafluoroethylene (Teflon) backbone, and may be considered to be a perfluorinated sulfonic acid resin. The combination of fluorinated backbone, sulfonic acid groups, and the stabilizing effect of the polymer matrix render Nafion® a very strong acid (i.e., superacid), with $H_o$(−11 to −13). Nafion® has various chemical configurations and thus several chemical names, including: ethanesulfonyl fluoride, 2-[1-[difluoro-[(trifluoroethenyl)oxy]methyl]-1,2,2,2-tetrafluoroethoxy]-1,1,2,2,-tetrafluoro-, with tetrafluoroethylene; and, tetrafluoroethylene-perfluoro-3,6-dioxa-4-methyl-7-octenesulfonic acid copolymer, for example. Nafion® is insoluble in non-polar solvents. It will be clear to those of skill in the art that polyacidic or heteropolyacidic catalysts other than MMT-K10, and perfluorinated sulfonic acid resins other than Nafion® NR50 may be suitable to facilitate the synthesis of pinene dimers, and the use of such other catalysts in the synthetic schemes disclosed are within the scope of this disclosure. For convenience in discussion, we refer herein to the sulfonated tetrafluoroethylene based fluoropolymer-copolymer incorporating perfluorovinyl ether groups terminated with sulfonate groups class of catalysts, suitable for use in synthesis of β-pinene dimer, including the Nafion® catalysts, as well as the acidic clays, simply as solid heterogeneous acidic catalysts or solid heteropolyacidic catalysts.

Diagram 2.
Structure of Perfluorinated Sulfonic Acid Resin Catalysts.

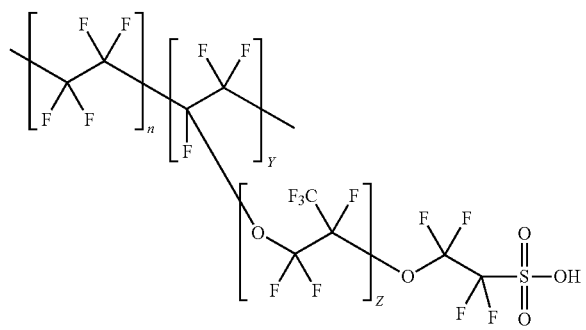

With respect to the catalysts of the structure shown in Diagram 2, the variables x, y, and z are mutually independent integers greater than 1. That is, any one of the variables x, y, z may have an integer value which is not dependent on the value of any other variable. Unlike MMT-K10 which maintains a high surface area and can delaminate at elevated temperature to yield easily dispersible nanosized catalyst particles, Nafion does not disperse well in non-polar solvents (Botella, P.; Corma, A.; López-Nieto, J. M. *J. Catal.* 1999 185, 371-377). This limits the surface area of the catalyst and the relative amount of active sites in contact with the reaction medium. Nafion can be well dispersed on inorganic supports including silica or alumina, but the presence of the support can often influence the reactivity and in the case of β-pinene may lead to more isomerization products and lower ring strain dimers (Kumar, P.; Vermeiren, W.; Dath, J.; Hoelderich, W. F. *Energy Fuels* 2006 20, 481-487). The catalyst was prepared by precipitation of a Nafion dispersion from water/alcohol and was dried under vacuum (4 mmHg) at ambient temperature to yield a flocculent white powder. In a manner similar to Amberlyst-15, Nafion showed virtually no reaction at room temperature for reaction times as long as 24 h. When neat solutions of β-pinene were heated with Nafion to 90° C. with stirring, no reaction occurred for an extended period of time, typically 20-50 minutes, and then without warning, the Nafion turned a dark red color and a rapid exothermic reaction ensued with evolution of gas. Upon an additional hour at 90° C., $^1$H NMR spectroscopy revealed that the only remaining low molecular weight molecules were camphene and a small amount of p-cymene. In fact when MMT-K10 was used as a catalyst nearly 10 times more p-cymene was produced. This result suggested that either the ring opening mechanism that converts β-pinene to limonene does not readily occur with Nafion at these reaction temperatures, or that the rate of dimerization of limonene over Nafion is substantially faster than the dehydrogenation reaction to produce p-cymene. To differentiate between the two possibilities, a reaction was stopped prior to completion and an NMR spectrum was collected. Camphene was the dominant monomeric olefin, with small, nearly equal amounts of β-pinene and limonene. At this point in the reaction, p-cymene was not observed in the $^1$H NMR spectrum. It appears from the data that the primary mechanism over Nafion is conversion to camphene concomitant with homo- and cross-dimerization of the olefin mixture. Upon further reaction it was observed that the last olefin remaining is camphene which dimerizes somewhat sluggishly over Nafion, however, unlike MMT-K10, continued reaction at 100° C. led to the conversion of camphene to dimer molecules. In order to determine the effect of temperature, the reaction was run neat at 140° C. using Nafion as the catalyst. Interestingly, p-cymene was formed in amounts similar to that observed for MMT-K10, in addition to the observance of about 10 wt % trimer. This suggests that for Nafion the dehydrogenation of limonene to p-cymene is favored at higher temperatures, while dimerization is favored at lower/intermediate temperatures. As with MMT-K10, it appears that a temperature of 100° C. is ideal for maximizing the amount of dimer produced. For all of the Nafion reactions, the catalyst could be removed by simple decantation and reused at least 3 times without significant loss of activity and given sufficient reaction time, yields of dimer as high as 90% were obtained. As mentioned previously, at the conclusion of the reaction the Nafion takes on a deep red hue. Washing the Nafion 5 times with $CH_2Cl_2$ did not remove the color, but only weak C—H stretches were observed in the IR spectrum of the washed and dried catalyst. With respect to FIG. 1, the GC/MS chromatogram of the product mixture revealed a broad distribution of dimer molecules with the majority having m/z=272. Small amounts of other molecular weights such as 274 and 288 were also observed, with the former being attributed to the coupling of terpinenes and menthenes and the latter attributed to isobornyl ether which has been shown to be an oxidation product produced from camphene with heteropolyacidic catalysts (Scheme 6) (Lana, E. J. L.; da Silva Rocha, K. A.; Kozhevnikov, I. V.; Gusevskaya, E. V. *J Molec. Catal. A* 2006 243, 258-263).

Upgrading of Dimer Mixtures

The dimer yield varied depending on the catalyst and conditions. Yields of dimer were reduced when MMT-K10 was utilized due to an increase in the amount of p-cymene produced and the inability of MMT-K10 to efficiently homodimerize camphene. The amount of dimer was also heavily influenced by the reaction temperature in that higher temperatures produced trimer molecules and potentially other higher oligomers. Reactions run at greater than 140° C. produced colored solutions ranging from dark yellow to orange-red depending on the reaction time, suggesting that polymeric or conjugated mixtures were being produced. Reactions controlled at about 100° C. with refluxing heptanes gave colorless mixtures when MMT-K10 was utilized as the catalyst and pale yellow mixtures when Nafion was utilized.

Scheme 6.
Acid catalyzed conversion of camphene to diisobornyl ether.

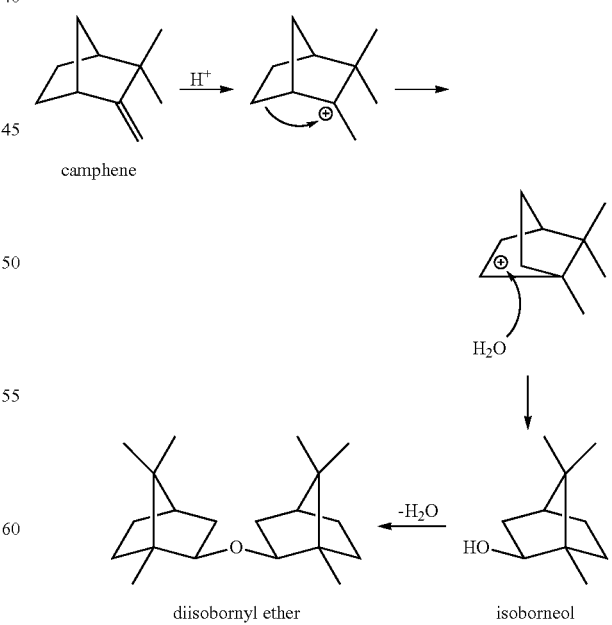

For potential use as fuels, these dimer mixtures must be hydrogenated to increase their stability. The reaction mixtures were simply decanted and transferred to another flask for hydrogenation; no workup or caustic treatment was required. Platinum dioxide ($PtO_2$) was utilized as the hydrogenation catalyst under mild $H_2$ pressures as it has been shown to be a very efficient catalyst for hindered olefins (Wright, M. E.; Harvey, Benjamin G.; Quintana, R. *Energy and Fuels* 2008, 22, 3299) (Harvey, B. G.; Wright, M. E.; Quintana, R. L. *Preprints of Symposia-ACS Div. Fuel Chem.* 2009 54 305-306). The resulting dimer mixtures were then placed under reduced pressure to remove n-heptane and low molecular weight products including camphane (MMT-K10 catalyst) and then vacuum distilled to produce a dimer cut. Fractional vacuum distillation gave a trace of a low boiling fraction consisting of primarily camphane, and p-cymene, followed by a colorless dimer fraction (bp 116-122° C., 4 mmHg) and leaving a small amount of resinous solid pot residue including a mixture of dimer and traces of other heavier oligomers. Isolated, distilled yields of the dimer fraction were greater than 80% on a 30 g scale, while for larger operations, a yield of up to 90% based on the GC/MS data seems reasonable due to more efficient distillations. Although higher oligomers limit the yield of dimer molecules they have uses in a variety of industries as resins and glues. (Goldschmidt, S.; McBride, J. J. in *Polymeric Materials Encyclopedia* Vol. 9; Salamone, J. C. Ed. CRC Press 1996 6878-6884). The properties of the fuel are listed in Table 3. The density of the hydrogenated dimer mixture prepared with Nafion was 0.938 g/cm$^3$, similar to JP-10 at 0.94 g/cm$^3$. The net heat of combustion of the dimer mixture was 141,745 BTU/gal, virtually identical to JP-10 (142,000 BTU/gal), while the pour point was determined to be −30° C., substantially higher than JP-10 with a freezing point of −79° C.

TABLE 3

Selected Properties of Hydrogenated Pinene Dimers.

| Property | Value |
| --- | --- |
| Density, g/cm$^3$ | 0.938 |
| Heating Value, MJ/L | 39.5 |
| (BTU/gal) | 141,745 |
| Pour Point, ° C. | −30 |
| Sulfur, ppm | 0.5 |
| Carbon, % | 87.72 (calc. for $C_{20}H_{34}$: 87.52) |
| Hydrogen, % | 12.12 (calc. for $C_{20}H_{34}$: 12.48) |

Given recent advances in the conversion of starch (Ramey, D. E. U.S. Pat. No. 5,753,474) and cellulosic biomass to biobutanol (Qureshi, N.; Sahaa, B. C.; Hector, R. E.; Hughes, S. R.; Cotta, M. A. *Biomass Bioenergy* 2008, 32 (2), 168-175. Qureshi, N.; Sahaa, B. C.; Cotta, M. A. *Biomass Bioenergy* 2008, 32 (2), 176-183), it was explored using the C4 alcohol as a pivotal and versatile starting point for the creation of new fuels. Because 1-butene can be easily derived from 1-butanol (Berteau, P.; Delmon, B.; Dallons, J. L.; Vangysel, A. *Appl. Catal.* 1991, 70 (2), 307-323. Bautista, F. M.; Delmon, B. *Appl. Catal., A* 1995, 130 (1), 47-65), this versatile starting material has been investigated as a precursors to a biojet fuel that will meet the required energy content and key performance specifications of JP-5. Disclosed herein are methods for converting 1-butene into a variety of useful saturated hydrocarbon fuels using a highly efficient batch-catalysis process. The new approach affords a product that is composed of 100% iso-paraffins, retains good fuel density, possesses attractive cold-flow properties, and can be easily tailored to have a high flash point.

The synthetic fuel experiments were initiated using the commercially available precatalyst bis(cyclopentadienyl)zirconium dichloride. The precatalyst is activated by treatment with a toluene solution of MAO followed by removal of the toluene under reduced pressure. The MAO may also be prepared in a solution of any aromatic solvent able to solvate the MAO and the precatalyst such as, without limitation, for example xylene, cumene, and mesitylene. Of course, coordinating solvents with heteroatoms are not appropriate. Removal of solvent after catalyst activation also removes any residual trimethylaluminum, creating "dried" MAO. The "dried" MAO has been shown to have a significant affect on catalyst activity for olefin oligomerization/polymerization reactions for several non-metallocene catalysts. (Hasan, T.; Ioku, A.; Nishii, K.; Shiono, T.; Ikeda, T. *Macromolecules* 2001, 34 (10), 3142-3145) (Hagimoto, H.; Shiono, T.; Ikeda, T. *Macromol. Rapid Commun.* 2002, 23, 73) (Furayama, R.; Saito, J.; Ishii, S.; Mitani, M.; Matsui, S.; Tohi, Y.; Makio, H.; Matsukawa, N.; Tanaka, H.; Fujita, T. *J. Mol. Catal. A: Chem.* 2003, 200, 31) (Long, R. J.; Gibson, V. C.; White, A. J. P. *Organometallics* 2008, 27 (2), 235-245). The catalyst was prepared using an aluminum/zirconium ratio of 100 (mol/mol). It may be noted that here the MAO is an oligomer of formula $[CH_3AlO]_n$, and there is one mole of aluminum for every mole of MAO repeat unit. Similarly, there is one mole of Zr per mole of $Cp_2ZrCl_2$. Conveniently, both the molar ratio of MAO/$Cp_2ZrCl_2$ and Al/Zr is 100:1. The turnover number (TON) here is at least about 17,000 and may be pushed to as high as on the order of $10^7$ whereas the TON achieved by Christoffers and Bergman was only about 10 or less. It is well known that use of very high Al/M ratios on the order of 10,000:1 results in the production of polymers, whereas significantly lower ratios can lead to oligomeric mixtures. Our use of the Al/M ratio of 100:1 is an approximate first optimization of the system based upon previous observations.

1-butene (375 mL, about 240 g) is condensed onto $CaH_2$ and then transferred over the course of 3 h to a chilled (dry ice bath) pressure reaction vessel containing "activated" catalyst. Reactions were performed in a Parr stainless steel pressure reaction vessel lined with a glass insert and stirring was accomplished using a Teflon coated stirring bar. The 1-butene [Specialty Gas Concepts, Lancaster, Calif., 98% Chemically Pure (CP) grade] was transferred after drying (over $CaH_2$) to the chilled reaction vessel through Tygon tubing. Once the pressure vessel was charged, the port was sealed, the cooling bath was removed, and the reaction vessel was kept at ambient temperature for 16 h (Scheme 7). At completion of the reaction, a partial vacuum exists in the reaction vessel. This observation is consistent with complete consumption of the 1-butene (bp −6.3° C.). Gas chromatography-mass spectrometry (GC-MS) analysis indicates a Schultz-Flory distribution of products consisting primarily of C8, C12, and C16 oligomers with small amounts of heavier oligomers. GC-MS analyses were performed using an Agilent 6890 gas chromatography (GC) system equipped with a Restek RTX-5MS 30 m column coupled to an Agilent 5973 mass selective detector system. After quenching as described herein below, a distillation using a vigreux column is used to remove the $C_8$ dimer, which accounts for about 25 wt % of the product mixture. Roughly 90% of the butene oligomer mixture consists of $C_8$ dimer and $C_{12}$, $C_{16}$, $C_{20}$, and $C_{24}$ oligomers, and there are essentially no oligomers larger than $C_{32}$. After removing the $C_8$ dimer, hydrogenation (about 0.08 wt % $PtO_2/H_2$, 2 psig) of the remaining oligomers yields a potential fuel mixture that has a flash point (ASTM D93) of 59° C., viscosity of 103 cSt (ASTM D445 at −20° C.), and a lubricity value of 0.45 mm [ASTM 6079, high frequency reciprocating rig (HFRR)]. All ASTM tests herein were performed at the Southwest Research Institute, San Antonio, Tex. 78238 (www.swri.org). Interestingly, this fuel does not show any sign of freezing (or cloudiness) when cooled to −60° C. When this fuel blend is subjected to a second high-temperature distillation, a colorless viscous oil residue is left behind that accounts for about 11% of the total fuel production. It is this oil fraction that leads to the good lubricity value for the fuel. It is important to note that incremental jumps are made in 4-carbon units, the reaction is highly regioselective based on GC-MS data, and the fuels generated in this process are 100% iso-paraffinic. The branching is quite distinctive in that ethyl groups are located at regular positions along the carbon main chain of the oligomer. Furthermore, not only does this fuel have extensive branching, it contains a mixture of diastereoisomers that are produced as a consequence of the chiral carbon centers (marked with an asterisk in Scheme 7) present at the branch points. The diastereoisomers have different physical properties (e.g., boiling point) and can be clearly observed in both the nuclear magnetic resonance (NMR) spectra and GC-MS chromatograms. For example, the hydrogenated tetramer has three chiral centers. Using the standard formula of 2n (where n is the number of chiral centers), the tetramer will have 8 possible stereoisomers. This consists of 4 pairs of enantiomers and 4 different diastereoisomers. Hence, after hydrogenation of the trimer and generation of a second chiral center, two major peaks in the GC-MS chromatogram are observed. This observation is consistent with the structures shown in Scheme 7 and the regiochemistry anticipated from the earlier work of Kaminsky (above) on the ZN-catalyzed reactions of 1-butene.

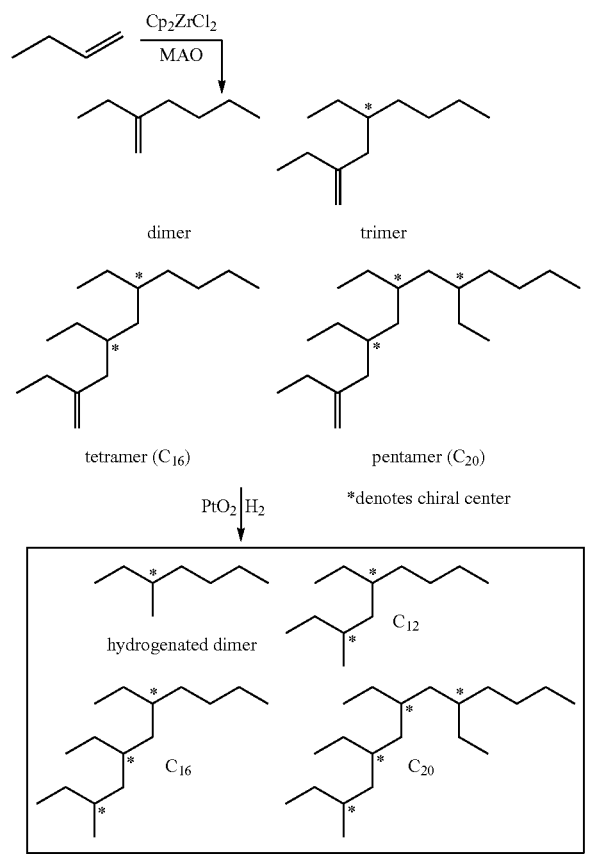

Scheme 7.

Figure 2:
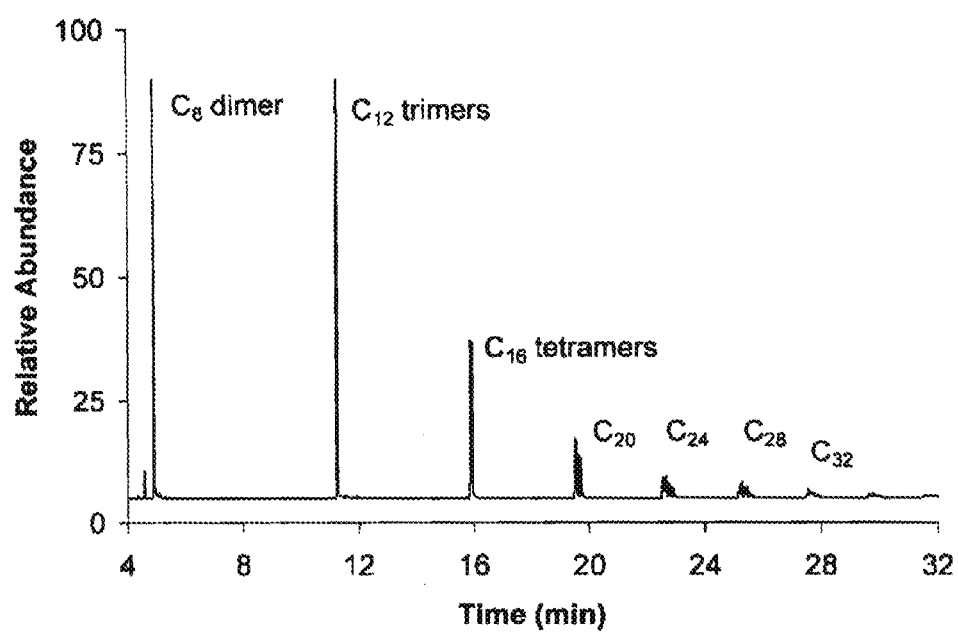
FIG. 2 is a plot of a GC-MS total ion chromatogram for the oligomers produced from 1-butene, according to embodiments of the invention.
Figure 3:
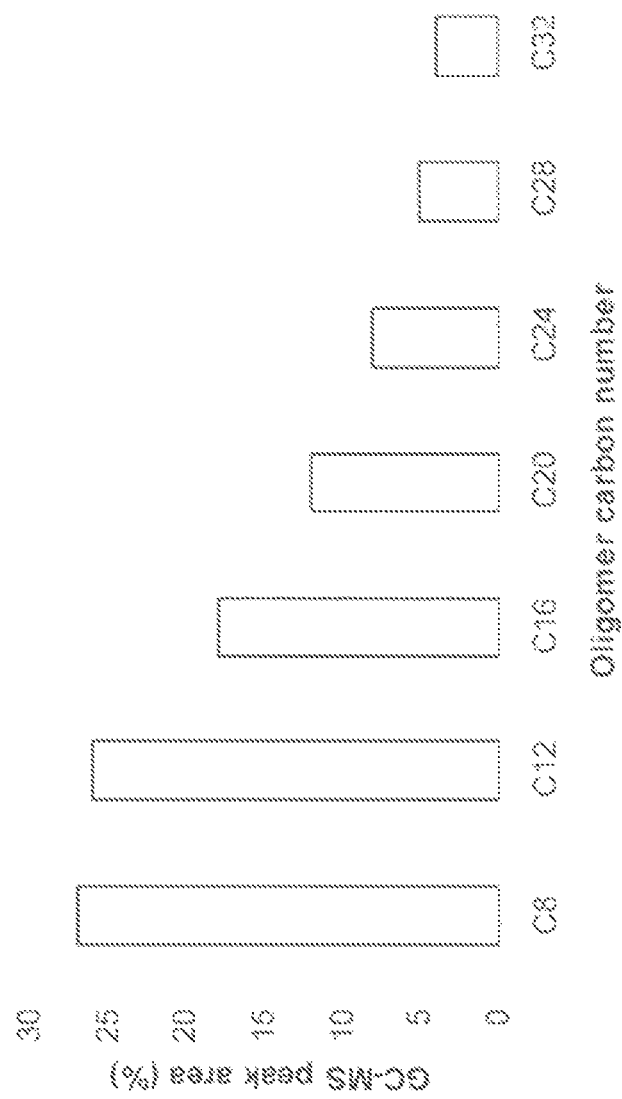
FIG. 3 is a graph of the relative area integration for each of the oligomers by carbon number for the GC-MS chromatogram of FIG. 2 above, according to embodiments of the invention.
Figure 4:
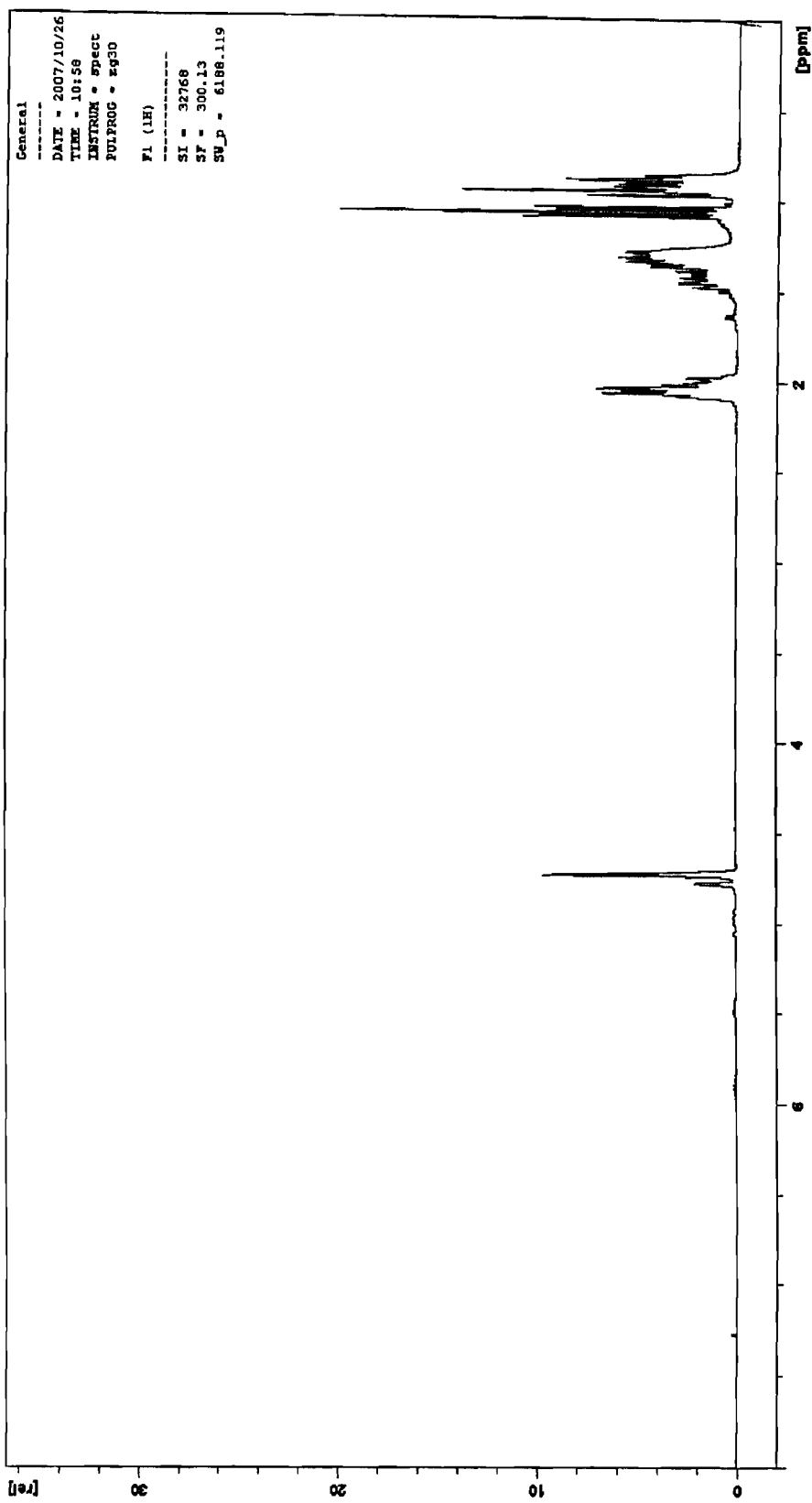
FIG. 4 is an $^1H$ NMR spectrum of butene oligomers, according to embodiments of the invention.
Figure 5:
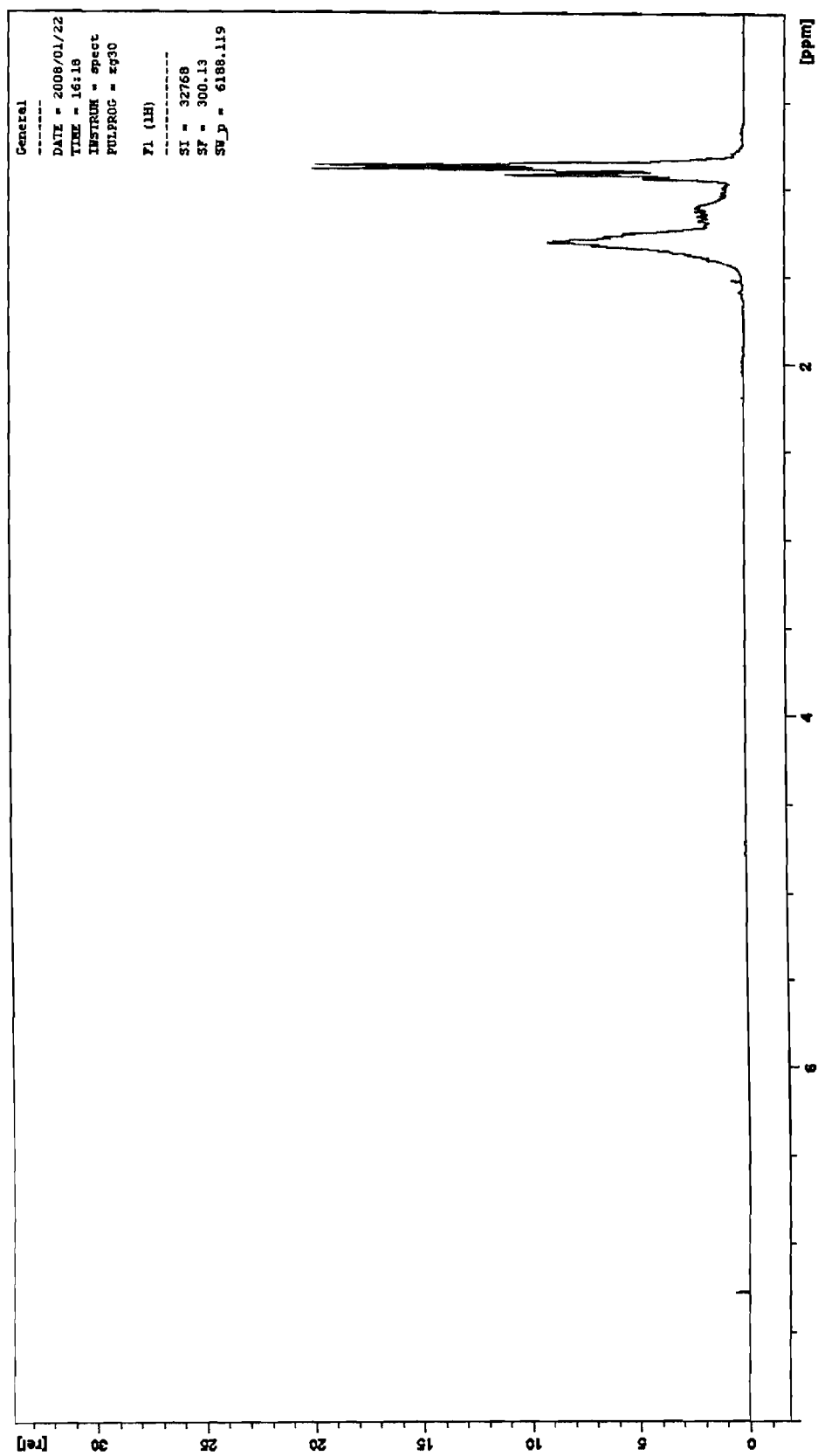
FIG. 5 is an $^1H$ NMR spectrum of hydrogentated butene oligomers, according to embodiments of the invention.
Figure 6:
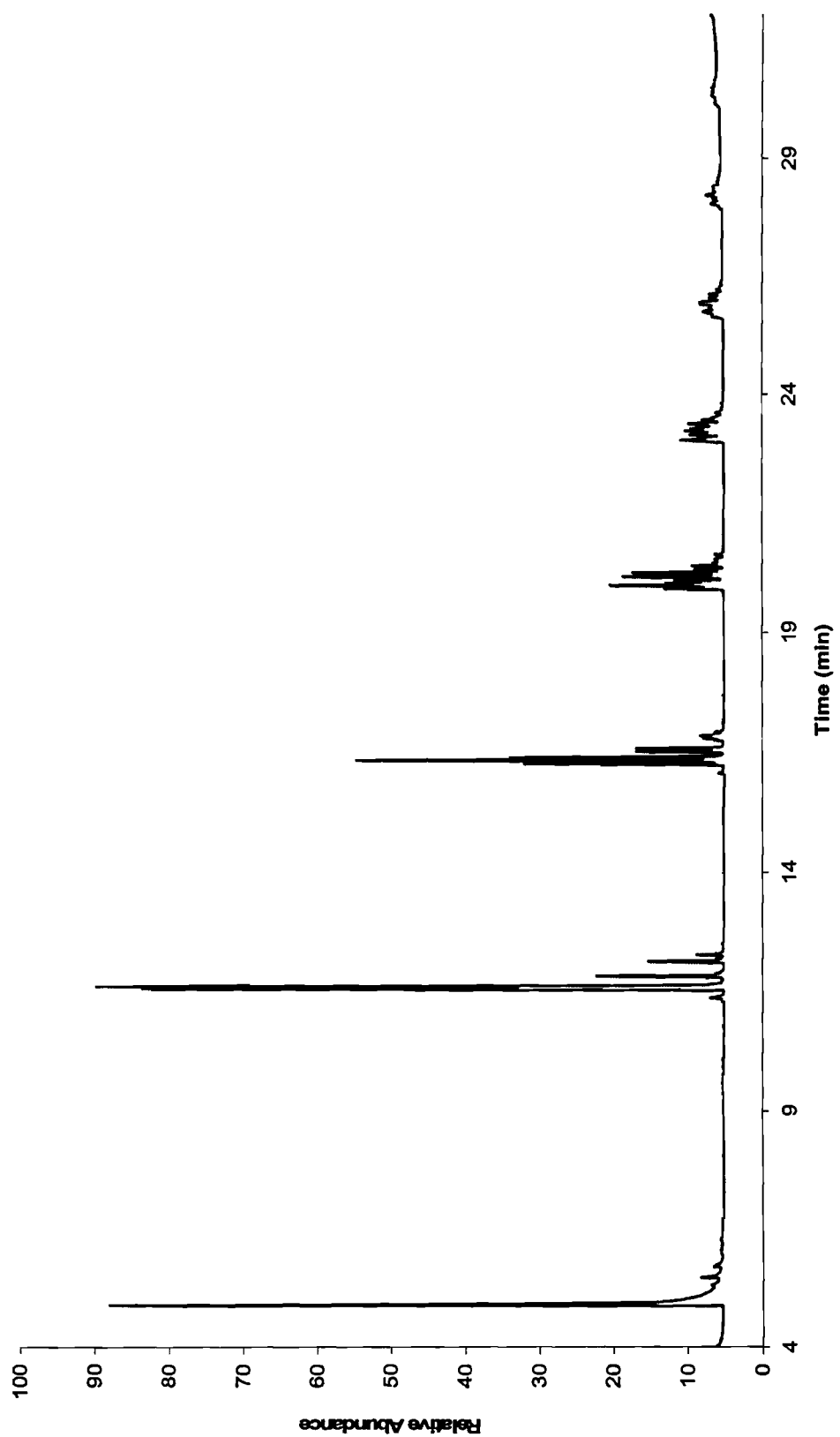
FIG. 6 is a Gas Chromatogram of hydrogenated butene oligomers, according to embodiments of the invention.
Figure 7:
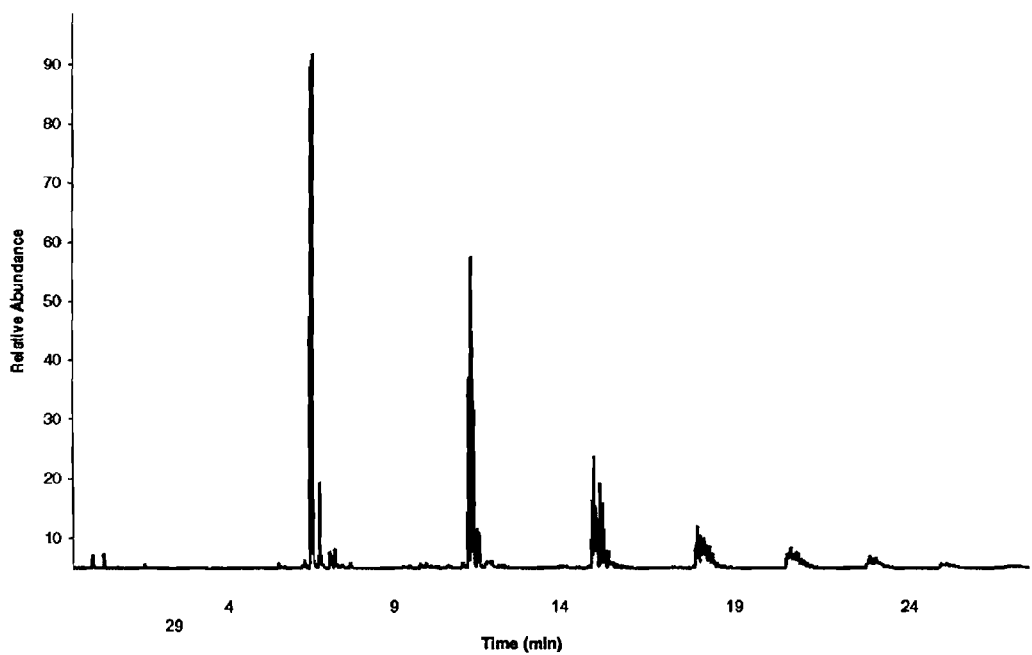
FIG. 7 is a Gas Chromatogram of distilled fuel, according to embodiments of the invention.

By making a change in catalyst preparation, we are able to produce a significant change in the resulting oligomer distribution toward lighter oligomers; however and importantly, the complete, or near complete, conversion of 1-butene remains unchanged. The catalyst is first formed in solution, then dried under vacuum and suspended in a small volume of hydrogenated butene dimer (3-methyl-heptane) derived from a previous run. This allows for reaction in which the solvent is primarily the reactant, 1-butene, without the need for addition of other solvent. This approach results in a mostly heterogeneous catalyst (i.e., the catalyst is dispersed in the solvent, but is not in solution, or is present in solution in only very low concentration). Using this heterogeneous, unsupported catalyst in the reaction results in a remarkable product distribution consisting primarily of dimer, trimer, and tetramer, but without production of heavy oligomers and polymer. This metallocene based unsupported heterogeneous catalyst method is a novel approach that results in a unique product distribution. It was discovered that if, after removal of the toluene, the aluminum/zirconium catalyst is slurried in hydrogenated dimer and then delivered to the reactor, the surprising result is: (1) complete, or essentially complete, conversion of 1-butene to oligomers as evidenced by a partial vacuum after completion of the reaction and the yield of oligomers obtained from the initial reactants; (2) an about 12 wt % increase in 2-ethyl-1-hexene dimer produced; and, (3) a decrease of high-molecular-weight oligomer generated, with the distribution defined by $M_n=176$, $M_w=211$, and $M_w/M_n=1.2$, where, $M_n$ is number average molecular weight, $M_w$ is weight average molecular weight, and $M_w/M_n$ is the polydispersity (FIG. 2). This distribution can be observed in FIG. 2 which is a plot of a GC-MS total ion chromatogram for the oligomers produced from 1-butene (Al/Zr: 100) using the catalyst made by removal of the toluene and delivering the zirconium/MAO as a slimy in hydrogenated dimer (3-methyl heptane). It will be understood by one of ordinary skill in the art that any lower molecular weight $C_4$ to about $C_{10}$ alkane may be used in place of 3-methyl-heptane, such as for example, butane, pentane, hexane, heptane, octane, and branched chain alkanes. FIG. 3 is a relative area integration for each of the oligomers by carbon number for the GC-MS chromatogram of FIG. 2. The relative abundance areas are derived from the total ion count for the peaks of that particular set of oligomers (e.g., $C_{24}$). Yields of 98% or more with some loss of product due to filtration, handling and transfer were obtained. This advantageously also enables the entire procedure to be performed using simple Schlenk techniques while avoiding using a glovebox. At this time, we do not completely understand the exact chemical differences/changes in the new active catalyst; however, the results are very consistent from run to run for this new catalyst preparation. As before, distillation is used to remove the 2-ethyl-1-hexene dimer, and the resulting fuel blend of oligomers minus the dimer is subjected to hydrogenation. Using the new catalyst formulation, we observe a significant decrease in viscosity, down to 12.5 cSt, (entry 1 in Table 3) compared to products prepared using our earlier catalyst formulation. The cold-flow viscosity by back-addition of hydrogenated $C_8$ dimer can be further tailored. Thus, by adding 6.6 wt % (entry 2 in Table 3) of the dimer, the viscosity decreases to 8.5 cSt, which is quite close to JP-8 (8.0 cSt) and does meet the JP-5 (8.5 cSt) specification. Further dilution with the $C_8$ dimer brings the

TABLE 3

| Viscosity Data (ASTM D445, −20° C.) for Fuel Blends[a] | | | |
|---|---|---|---|
| fuel blend | viscosity (cSt) | dimer (%) | fuel density (g/mL) |
| 1 | 12.5 | 0 | 0.78 |
| 2 | 8.5 | 6.6 | 0.77 |
| 3 | 7.2 | 11.5 | 0.77 |
| 4 | 6.0 | 17 | 0.76 |

[a] Catalyst delivered as a slurry in hydrogenated dimer.

viscosity down to an impressive 6.0 cSt at −20° C. (entry 4 in Table 3). As anticipated, there is a decrease in fuel density as the dimer concentration increases.

Carrying out a high-temperature distillation of the high flashpoint fuel mixture (no dimer) to 313° C. leaves a colorless pot residue of less than 1 wt % and physically/experimentally confirms the decrease in high-molecular-weight oligomer content. For the fuel blend of entry 1 in Table 3, elemental analysis indicates 85% carbon and 15 wt % hydrogen, which is consistent with a fully saturated hydrocarbon. It follows that the calculated heat of combustion is greater than 44+ MJ/kg or 34.3+ MJ/L. The heat of combustion is calculated for the stoichiometric reaction with oxygen to form carbon dioxide and water using an average formula of $C_{16}H_{34}$. The elemental analysis was performed at Atlantic Microlab, Inc., Atlanta, Ga.

Figure 8A:
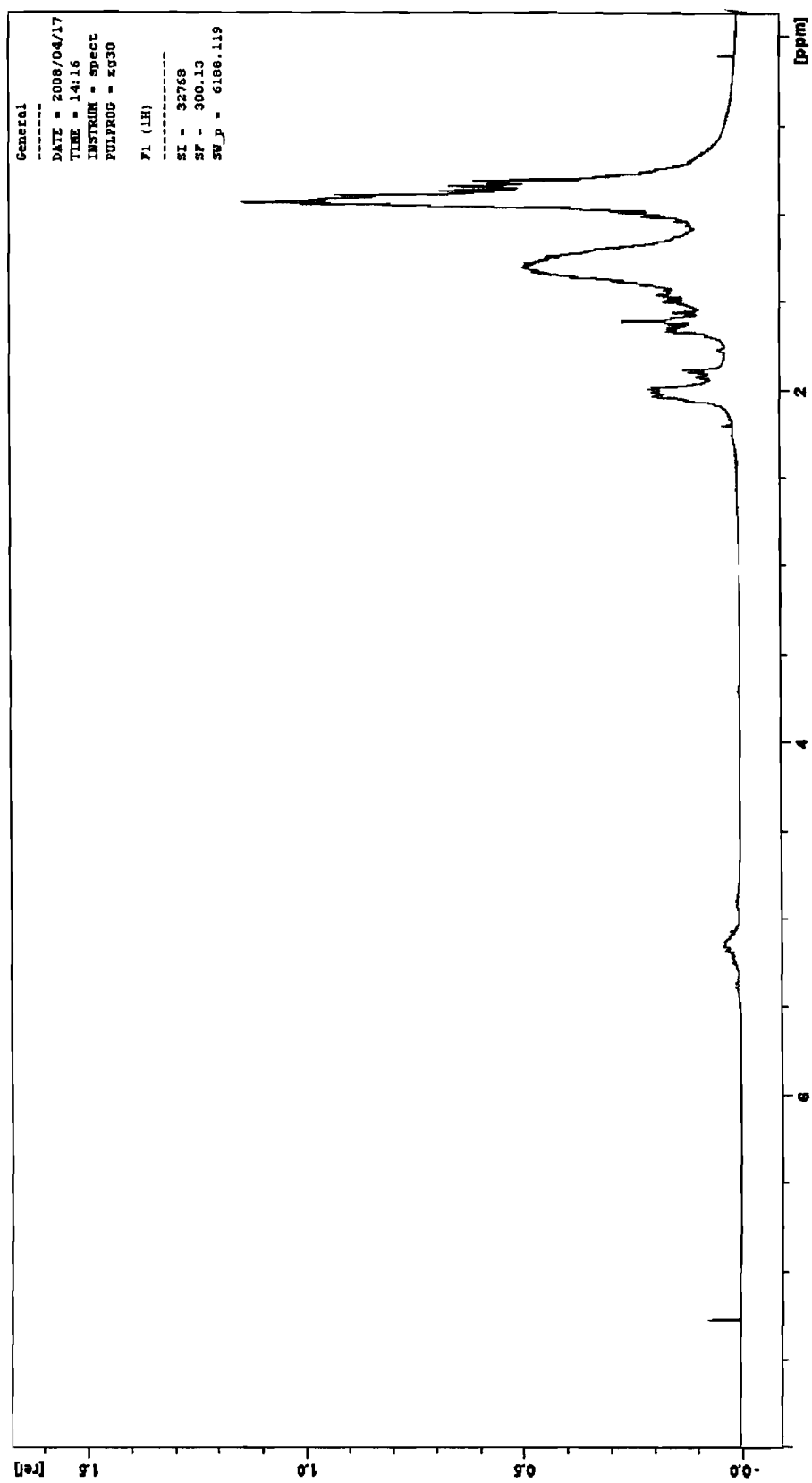
FIGS. 8A and 8B are a $^1H$ and $^{13}C$ NMR spectra of the product mixture derived from sulfuric acid dimerization of 2-ethyl-1-hexene, according to embodiments of the invention.
Figure 8B:
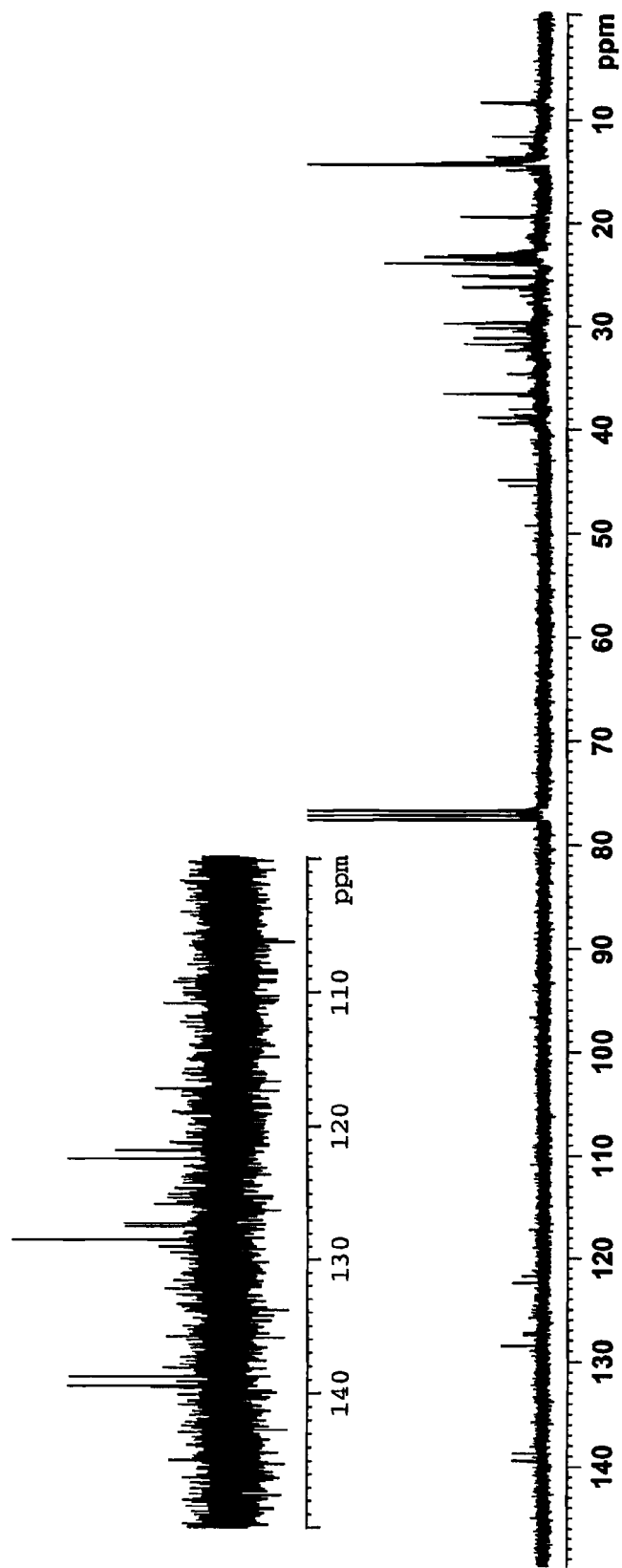
Figure 9:
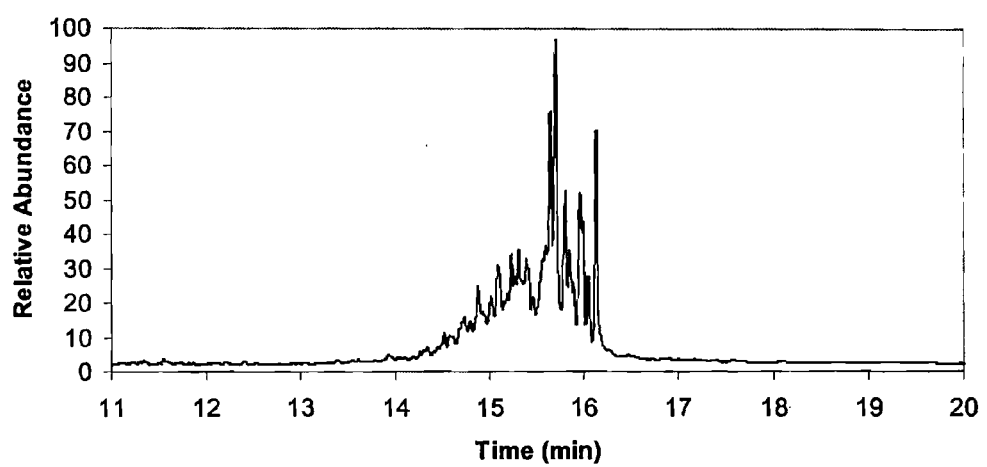
FIG. 9 is a gas chromatogram (GC) of 2-ethyl-1-hexene dimers, according to embodiments of the invention.

To demonstrate an overall efficient use of the reduced-carbon source (i.e., 1-butene), a means of converting the dimer (2-ethyl-1-hexene) to a higher boiling fuel component [e.g., $C_{16}$ compound(s)] was sought. The latter could then be blended with little negative effect on the flash point of the fuel. Thus, treatment of 2-ethyl-1-hexene with concentrated sulfuric acid leads to rapid conversion to a complex mixture of monounsaturated $C_{16}$ alkenes (Scheme 8). FIG. 9 is dimerized 2-ethyl-1-hexene, but by Nafion, not sulfuric acid. The proton and carbon NMR spectral data for the product mixture are quite complicated (FIG. 9); however, the GC-MS data (FIG. 8) is consistent with an elution time that is expected for $C_{16}$ isomers, and most importantly, a molecular ion peak of 224 is observed for each peak in the GC-MS chromatogram, with very small amounts of 238 molecular ions ($C_{17}$ alkenes) indicated.

The mixture of $C_{16}$-alkene isomers has a measured density of about 0.80 g/mL that is similar to pure linear n-hexadecane (0.773 g/mL). One of the unique and useful features for these 1-butene derived fuels is the high degree of branching (100%) yet a good overall retention of fuel density. Although a cetane rating for jet fuels is not specified nor directly related to any performance parameter, there is interest to further evaluate these fuels for their respective cetane and octane ratings. Extensive and regular ethyl branching is not typically found in fuel blends; therefore, an appropriate model for predicting a cetane rating is not presently available. Fuel density is an important parameter that contributes to meeting fuel performance requirements and may ultimately determine if a biojet version of JP-5/JP-8 can indeed meet or exceed mission critical Department of Defense (DoD) requirements.

Scheme 8.

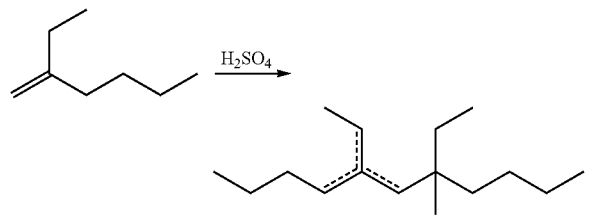

Experimental

General Methods. All organometallic manipulations were carried out using standard Schlenk techniques under an atmosphere of purified nitrogen or in a glovebox. 1-butene (CP grade) was purchased from Specialty Gas Concepts, stirred over $CaH_2$, and degassed prior to use. MAO (10% in toluene) and $PtO_2$ were purchased from Aldrich and used as received. $Cp_2ZrCl_2$ was purchased from Strem and used as received. Butene oligomerization reactions were conducted in a 750 mL stainless steel Parr reactor fitted with a glass insert. $^{1}H$ and $^{13}C$ NMR spectra were collected on a Bruker Avance II 300 MHz spectrometer in $CDCl_3$ and referenced to the residual solvent peaks ($^{1}H$, δ 7.27; $^{13}C$, δ 77.16). Fuel samples were analyzed for viscosity (ASTM D445 at −20° C.), lubricity (ASTM D6069, HFRR), and flashpoint (ASTM D93) at Southwest Research Institute.

GC/MS Analysis Methods. 0.5 mg of oligomer mixture was dissolved in 1.0 mL of methylene chloride. 1 μL of sample was injected into an Agilent 6890 gas chromatography (GC) system equipped with a Restek RTX-5MS 30-meter column. The GC inlet temperature was 250° C., the initial column temperature was 40° C. held at 3 min, and the temperature was increased at 10° C./min up to a final temperature of 350° C. An Agilent mass selective detector 5973 system was used to identify the sample components.

Synthesis of Butene Oligomers (Method A). Utilizing Schlenk techniques, $Cp_2ZrCl_2$ (70 mg, 0.24 mmol) was dissolved in MAO solution (16.5 mL, 25 mmol) to yield a pale yellow solution which was stirred at ambient temperature for 1 h. The resulting golden colored solution was then stripped of solvent under reduced pressure (0.1 mm Hg) to give a yellow solid. The flask was taken into a glovebox and the solid transferred to a bomb. The bomb was then removed from the glovebox and packed in dry ice. 1-butene (375 mL, 4.22 mol) was condensed into the bomb which was sealed, placed on a stir plate, allowed to warm to room temperature, and allowed to react for 16 h with stirring. A port on top of the bomb was opened (with a nitrogen purge) and this released a significant partial vacuum due to the complete conversion of butene to oligomers. The catalyst was quenched with distilled water (1 mL) and the mixture was stirred for 1 h. The top portion of the bomb was completely removed to reveal a white heterogeneous mixture smelling strongly of olefins. This mixture was filtered through a short plug of basic alumina (2 cm) and glass wool to yield 230 g (97%) of butene oligomers.

Synthesis of Butene Oligomers (Method B). The activated catalyst solution was prepared as above. The solvent was removed under reduced pressure (0.1 mm Hg) and dry 3-methyl heptane (10 mL), was added to the flask with vigorous stirring to form a pale yellow slurry that was then transferred via a syringe into the bomb. The oligomerization reaction was then carried out as above. Yields were similar to Method A.

Hydrogenation of Butene Oligomers. Butene oligomers (400 g) were placed in a 3-neck flask with a gas outlet. The solution was degassed and the atmosphere was replaced with nitrogen. $PtO_2$ (400 mg, 1.76 mmol) was added and the mixture was placed under a continuous hydrogen pressure of 2 psig. One of ordinary skill in the art will understand that butene oligomers may also readily be hydrogenated under pressure using nickel catalysts. The reaction could be conveniently monitored by NMR spectroscopy, but flocculation of the catalyst occurred upon completion of the reaction and was subsequently used to determine the end point. After 24 h the reaction mixture was filtered through glass wool to give a quantitative yield of colorless liquid.

Dimerization of 2-ethyl-1-hexene. A flask was charged with sulfuric acid (98%, 0.3 mL) and 2-ethyl-1-hexene (4.45 g, 40 mmol) in that order. There was an initial exotherm upon mixing. The heterogenous mixture was allowed to react with stirring at ambient temperature for a period of 16 h. The colorless organic layer was separated and washed with aqueous $Na_2CO_3$ solutions (3×3 mL), followed by distilled water (3 mL) and analyzed by GC/MS, $^{1}H$ and $^{13}C$ NMR spectroscopy. Most of the peaks observed by GC/MS have molecular ion peaks of 224 and eluted in the range of 15-17 min, suggesting that primarily dimerization had taken place without a significant amount of cracking. The NMR spectra of the mixture were complex due to the formation of several isomers, yet the ratio of aliphatic protons to olefinic protons determined by NMR spectroscopy was consistent with an average formulation of $C_{16}H_{32}$ based on the assumption that primarily tri-substituted olefins were formed by the acid catalysis.

By tuning the catalyst and then using the dimer produced, it can bring the carbon use to about 95% or greater. This latter point will be particularly important in the future, where the source of raw materials (i.e., biomass/biofeedstock) is limited. Also noteworthy, the batch catalysis approach herein requires a minimal input of energy and hydrogen to make fuels that possess useful flash points, excellent cold flow properties, and high solution density/energy content. This new process affords a saturated hydrocarbon fuel that has a higher solution density and thus possesses a higher calculated power density (per volume) than similar fuels made by the GTL Fischer-Tropsch processes.

Embodiments of the invention include the conversion of a significant byproduct of 1-butene oligomerization into a hydrocarbon mixture suitable as a stand-alone or component of both turbine and diesel fuel.

Embodiments include a selective and high yielding (90+%) method for dimerizing 2-ethyl-1-hexene to a complex hydrocarbon mixture, utilizing environmentally favorable solid acid catalysts. Embodiments described in related applications detailed a method for producing a JP-5 equivalent fuel from 1-butene. As 1-butene can be derived from butanol which can be derived from biomass, this permits an efficient process to convert biomass to full performance jet fuels. The related process converts 98% of the 1-butene into oligomers, with ca. 40% of the product mixture composed of 2-ethyl-1-hexene. The flashpoint of this latter compound is too low to incorporate into JP-5 mixtures (flashpoint: 60° C.), although JP-8 mixtures (flashpoint: 38° C.) may include up to ca. 15% of this hydrocarbon. To improve the overall yield of jet fuel range hydrocarbons, methods to selectively dimerize 2-ethyl-1-hexene were investigated. This renewable fuel can be used as either a stand-alone fuel or can be blended back in with the butene oligomer (JP-5 equivalent) fuel. In either case, the effective dimerization of 2-ethyl-1-hexene permits for a 1-butene to jet fuel conversion of >90%.

An efficient method for the selective dimerization of the renewable feedstock, 2-ethyl-1-hexene, to a complex mixture of $C_{16}H_{32}$ hydrocarbons is described below in this patent application. To optimize the process, the activity of a variety of strongly acidic heterogeneous catalysts was investigated. Montmorillonite K-10 and sulfated zirconia readily isomerized 2-ethyl-1-hexene to a mixture of the cis- and trans-isomers of 3-methyl-2-heptene and 3-methyl-3-heptene, but were inactive for the dimerization of 2-ethyl-1-hexene at temperatures up to 116° C. In contrast, the cation exchange resins Amberlyst-15 and Nafion, readily dimerized 2-ethyl-1-hexene at elevated temperatures. For both sets of catalysts, the degree of hydration strongly affected the rate of isomerization/dimerization. After hydrogenation over $PtO_2$ and fractional distillation, saturated dimer mixtures could be isolated in up to 90% yield. The dimers have a density of 0.78 g/mL and a freezing point <−60° C., suggesting that they can be blended with renewable or conventional jet fuels, without adversely affecting the overall density and low temperature viscosity of the mixtures.

Given current concerns about diminishing oil reserves and the potential impact of global warming, research into renewable fuels has been accelerating. Many critics of renewable fuels correctly point out that current fuels such as corn-based ethanol and soybean based biodiesel represent unsustainable approaches to large scale production of alternative fuels. For example, life cycle analysis of corn-based ethanol suggests that its use as a transportation fuel produces more net $CO_2$ than does gasoline when land use change is included in the calculation (Charles, D. Science 2009, 324, 587; Searchinger, T.; Heimlich, R.; Houghton, R. A.; Dong, F.; Elobeid, A.; Fabiosa, J.; Tokgoz, S.; Hayes, D.; Yu, T. Science 2008, 319, 1238-1240). These arguments coupled with impacts on global food prices are driving research into cellulosic biofuels. Ethanol produced from waste or non-food cellulose will result in up to 80% lower $CO_2$ emissions compared to gasoline. (Durre, P. Biotech. J. 2007, 2, 1525-1534). Despite this, ethanol has several shortcomings as a transportation fuel. Ethanol has only ⅔ the net heat of combustion of gasoline, is volatile, hygroscopic, and much more corrosive than hydrocarbon fuels.

A higher alcohol including biobutanol has several advantages over ethanol. Butanol has a higher flashpoint, is less corrosive, is easier to separate from water, and can be transported in existing pipelines. (Dune, P. Biotech. J. 2007, 2, 1525-1534). Perhaps most importantly, butanol has roughly 135% the volumetric heating value of ethanol, allowing it to be used as a direct replacement for gasoline in automobiles with virtually no change in gas mileage or performance. Biobutanol can be blended with conventional diesel and biodiesel fuels (Chotwichien, A.; Luenguaruemitchai, A.; Jai-In, S. Fuel 2009, 88, 1618-1624; Karabektas, M.; Hosoz, M. Renew. Energy 2009, 34, 1554-1559; Dunn, R. O. J. Am. Oil Chem. Soc. 2002, 79, 709-715) and has been shown to work well in diesel engines when combined with its partial dehydration product dibutyl ether. (Wright, M. E.; Harvey, B. G.; Quintana, R. L. Prepr. Pap.-Am. Chem. Soc., Fuel Div. 2008, 53, 252-253). The versatility of butanol suggests that it has the potential to be an important central feedstock for a variety of fuel products including gasoline, diesel, and saturated fuel precursors (Scheme 9).

Scheme 9. Butanol as a versatile central material for biofuel production

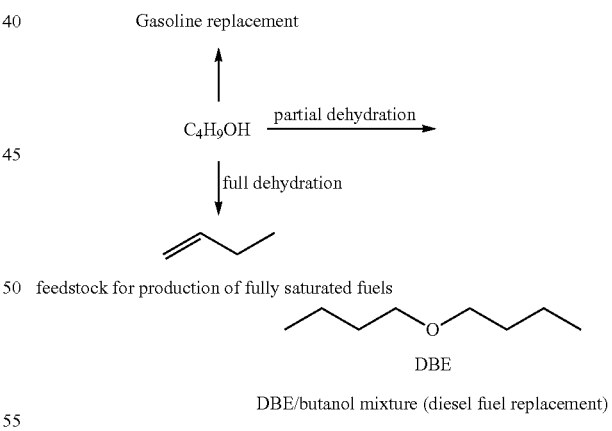

Although butanol has potential as an automobile fuel, it has limited use as a high performance military fuel due to its relatively low flashpoint and the presence of oxygen which limits its net heat of combustion. Earlier it was shown that a fully saturated fuel mixture can be obtained through the oligomerization of 1-butene, followed by hydrogenation. (Wright, M. E.; Harvey, B. G.; Quintana, R. L. Energy Fuels 2008, 22, 3299-3302). As 1-butene can be derived from biobutanol through dehydration, this process allows for the synthesis of high performance jet and diesel fuels from renewable sources. The oligomerization is carried out with the use of a Ziegler Nana catalyst system and produces primarily 1,2-insertion products (Scheme 9). The optimized process for the synthesis of fuel range oligomers (C12, C16) without concomitant production of heavy oligomers can yield up to 40 mass % dimer. To develop an efficient method to incorporate dimer into the overall fuel mixture without adversely affecting the flash point, methods to dimerize 2-ethyl-1-hexene, followed by hydrogenation, to produce $C_{16}H_{34}$ molecules were investigated (Scheme 10).

Scheme 9.
Synthesis of butene oligomers with a Ziegler Natta catalyst

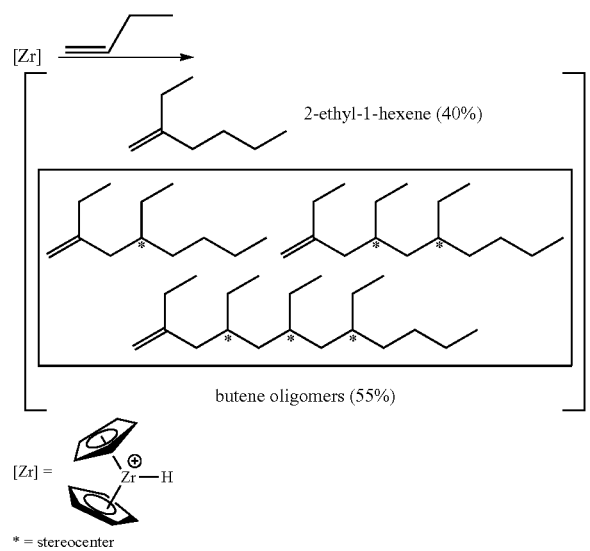

* = stereocenter

Scheme 10.
Acid catalyzed dimerization of 2-ethyl-1-hexene
for the synthesis of renewable jet fuel.

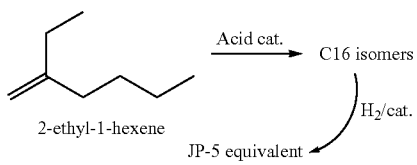

Many catalysts promote the dimerization of alpha olefins; however, 1,1-disubstituted and especially unactivated 1,1-disubstituted olefins including 2-ethyl-1-hexene present a challenging target. Strongly acidic catalysts such as $H_2SO_4$ and HF are used industrially as alkylation and dimerization catalysts to produce high octane fuel additives from isobutylene raffinate. However, sulfuric and hydrofluoric acids are corrosive, dangerous to work with, and require energy intensive recycling processes. (Sheldon, R. A.; Downing, R. S.; Applied Cat. A. 1999, 189, 163-183; Kumar, P.; Vermeiren, W.; Dath, J.; Hoelderich, W. F. Energy Fuels 2006, 20, 481-487). Liquid superacid catalysts, including triflic acid, can also be used for alkylation and addition reactions, yet they can often lead to unproductive cracking reactions (Olah, G. A.; Batamack, P.; Deffieux, D.; Török, B.; Wang, Q.; Molnar, A.; Prakash, G. K. S. Applied Catalysis A: General 1996, 146, 107-117) that may result in lower overall yields of dimers. Solid acid catalysts, including sulfated zirconia, acid treated clays, and cation exchange resins, may offer the ability to selectively dimerize challenging olefins including 2-ethyl-1-hexene while limiting cracking reactions and offering additional benefits such as easy separation and minimal work-up.

Nafion (5% water alcohol dispersion), Montmorillonite K-10 (MMT-K10), and dry Amberlyst-15 were purchased from Aldrich. Dowex HCR-W2 (hydrated cation exchange resin) was purchased from J. T. Baker. Sulfated zirconia was prepared from $ZrOCl_2$-$8H_2O$ by a published method. (Song, S. X.; Kydd, R. A. J. Chem. Soc. Faraday Trans. 1998, 94, 1333-1338) Nafion was precipitated from its dispersion by addition of $CH_2Cl_2$ and ether, followed by filtration and drying under vacuum (1 Torr) at ambient temperature. (Kim, T. K.; Kang, M.; Choi, Y. S.; Kim, H. K.; Lee, W.; Chang, H.; Seung, D. J. Power Sources 2007, 165, 1-8). MMT K-10 was dried under vacuum (1 Torr) at 140° C. for 5 h. Dry Amberlyst-15 and Dowex HCR-W2 were used directly from the bottle. 2-Ethyl-1-hexene was prepared from 1-butene and was distilled from $CaH_2$ prior to use. Its purity was >99% with trace amounts of 3-methylheptane present. All reactions were performed under a nitrogen environment. All NMR data were collected on a Bruker Avance 11300 MHz spectrometer. Product mixtures were analyzed with an Agilent 6890-GC/5973-MS to determine chemical compositions. 2-Ethyl-1-hexene was dimerized with a variety of heterogenous catalysts and sulfuric acid solutions (Table 4). Typical reaction conditions ranged from ambient temperature up to the reflux temperature of 2-ethyl-1-hexene (typical examples are presented below). Dimer mixtures were upgraded through decantation followed by hydrogenation with 1 wt % $PtO_2$ under 1-2 psig of hydrogen for a period ranging from 12-24 h. Subsequent distillations were carried out under a nitrogen atmosphere at atmospheric pressure.

TABLE 4

Catalysts for the Selective Dimerization of 2-ethyl-1-hexene.

| Catalyst | T (° C.) | Time | Products | Dimer Yield (%) | Conversion (%) |
|---|---|---|---|---|---|
| $H_2SO_4$ (98%) | 0 | 0.5 | dimer/oligomers | 90 | 100 |
| $H_2SO_4$ (66%) | 0 | 2 | isomers | 0 | —[a] |
| $H_2SO_4$ (66%) | ambient | 18 | isomers | 0 | 98 |
| MMT-K10 (wet) | ambient | 48 | isomers | 0 | 14 |
| MMT-K10 (wet) | 116 | 2 | isomers | 0 | 90 |
| MMT-K10 (dry) | ambient | 24 | isomers | 0 | 30 |
| MMT-K10 (dry) | 116 | 2 | isomers | 0 | 96 |
| Sulfated $ZrO_2$ | ambient | 24 | isomers | 0 | 19 |
| Sulfated $ZrO_2$ | 116 | 2 | isomers | 0 | 96 |
| Amberlyst-15 | ambient | 24 | starting material | 0 | 0 |
| Amberlyst-15 | 116 | 2 | dimer/oligomers | 70 | 98 |
| Nafion | ambient | 24 | starting material | 0 | 0 |
| Nafion | 116 | 2 | dimer/oligomers | 90 | 100 |

[a]not determined 2-ethyl-1-hexene dimerization (sulfuric acid). 2 mL of concentrated sulfuric acid was placed in a 3-necked flask equipped with a teflon coated stir bar, nitrogen inlet and pressure equalizing addition funnel. The flask was chilled in an ice bath and 10 mL of 2-ethyl-1-hexene was added dropwise. The mixture turned pale yellow and was vigorously stirred at 0° C. for an additional 30 min. Upon sitting, the mixture separated into two phases and was transferred to a centrifuge tube. The organic layer was syringed away from the acid layer and was stirred with an aqueous NaHCO$_3$ solution. The washing process resulted in a thick white emulsion that took several hours to separate. Addition of brine led to a clear organic layer, but subsequent water washes reproduced the emulsion. Attempts to reduce the dimers with Pd/C and PtO$_2$ under 1-2 psig H$_2$ were unsuccessful.

Heterogeneous catalysts (Nafion). 200 mg of dried, powdered Nafion was placed in a 3-necked flask equipped with a reflux condenser and 10 mL of 2-ethyl-1-hexene was added under nitrogen. The mixture was vigorously stirred and heated to the reflux temperature of 2-ethyl-1-hexene (116° C.) in an oil bath. The reaction was periodically monitored by NMR to determine the conversion to dimer molecules. The reaction was allowed to proceed for 2 h and was then cooled to room temperature. The dimer mixture was then separated by decantation to yield a pale yellow solution containing primarily dimer molecules (ca. 90% by GC/MS). After hydrogenation, fractional distillation gave a colorless dimer fraction.

In a recent paper initial results were reported showing that sulfuric acid is an effective catalyst for the facile room temperature conversion of 2-ethyl-1-hexene to a complex mixture of dimers. (Wright, M. E.; Harvey, B. G.; Quintana, R. L. *Energy Fuels* 2008, 22, 3299-3302). The bulk of the sulfuric acid could be easily removed by decantation, but caustic washes often led to emulsions that were difficult to resolve and the isolated C16 olefins proved difficult to hydrogenate, potentially due to poisoning of the catalyst by sulfonates. The sulfuric acid layer was highly colored suggesting that polar conjugated or polymeric species were being formed as side products. To determine if lower temperatures would allow for a more selective process, the reaction was carried out at 0° C. The acid layer turned pale yellow, suggesting that less side reactions were occurring, but the organic fraction was difficult to work-up as observed before. The use of less concentrated solutions (66%) produced only isomerization products with no dimerization. This result suggested that strongly acidic catalysts were necessary to induce the dimerization reaction. The use of sulfuric acid as a catalyst had several negative aspects, for example, large volumes of sulfuric acid (5/1, v/v, alkene/H$_2$SO$_4$) were required for the reaction to go to completion. Additionally, used acid solutions had limited activity and could not be easily recycled.

To simplify the dimer isolation process, reduce the amount of catalyst, and improve the susceptibility of the olefin mixture to hydrogenation, the use of heterogeneous acid catalysts for the selective dimerization of 2-ethyl-1-hexene were investigated. Several solid acid catalysts, including inorganic and polymer bound systems, were utilized. The solid acids (Table 5) included sulfuric acid treated montmorillonite clay (MMT-K10), a cross-linked polystyrene based hydrated cation exchange resin (Dowex HCR-W2), a macroreticular cation exchange resin (Amberlyst-15), sulfated zirconia, and Nafion (a perfluorinated sulfonic acid resin). MMT-K10 which has been utilized for the dimerization of activated olefins such as 1,1-diphenylethene, (Madhavan, D.; Murugalakshmi, M.; Lalitha, A.; i, K. *Catalysis Letters* 2001 73, 1-4) and more recently, β-pinene and its ring opened isomers, (Harvey, B. G.; Wright, M. E.; Quintana, R. L. *Preprints of Symposia-ACS Div. Fuel Chem.* 2009, 54, 305-306) was used without modification in a dimerization reaction. At room temperature, no reaction occurred, while at the reflux temperature (116° C.) complete isomerization to a mixture of 4 isomers was observed (Scheme 11).

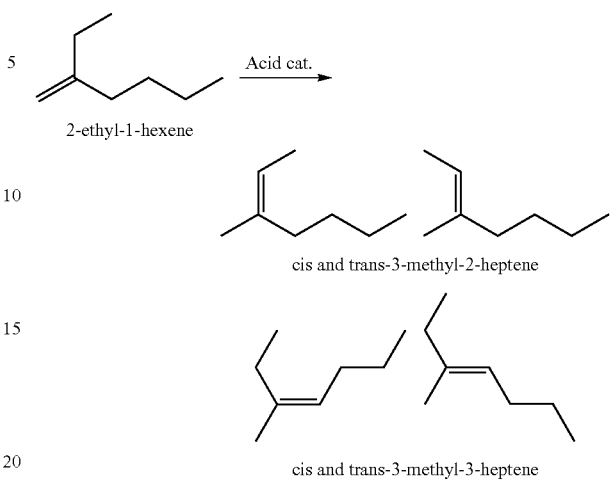

Scheme 11. Acid catalyzed isomerization of 2-ethyl-1-hexene.

The products consisted of the cis- and trans-isomers of 3-methyl-2-heptene and 3-methyl-3-heptene as confirmed through both NMR spectroscopy and GC-MS. The Hammett acidity of MMT-K10 can be drastically affected by the amount of water present, with wet MMT-K10 having H$_0$=(+3.3 to +1.5) and dry MMT-K10 (5 h 140° C., in vacuo) having H$_0$=(−5.5 to −8.2). (Pillai, S. M.; Ravindranathan, M. *J. Chem. Soc. Chem. Commun.* 1994, 1813-1814) Suitably dried MMT-K10 was utilized as a catalyst and revealed the ability to slowly isomerize 2-ethyl-1-hexene at room temperature but provided similar results to wet MMT-K10 at reflux temperatures and led to no dimerization products. Sulfated zirconia, which is an active catalyst for alkylation reactions and is often considered to have acidity comparable to sulfuric acid(Yadav, G. D.; Nair, J. J. *Microporous Mat.* 1999, 33, 1-48; Valyon, J.; Onyestyak, G.; Lonyi, F.; Barthos, R. *J. Phys. Chem. B* 2000, 104, 7311-7319; Umansk, B.; Engelhardt, J.; Hall, W. K. *J. Catal.* 1991, 127, 128; Busca, G. *Chem. Rev.* 2007, 107, 5366-5410), was prepared from ZrOCl$_2$-8H$_2$O and was shown to have similar behavior to MMT-K10 in that it reacted slowly with 2-ethyl-1-hexene at room temperature and led solely to isomerization at the reflux temperature.

TABLE 5

Selected Properties of Solid Acid Catalysts.

| Catalyst | Surface area (m$^2$/g) | Hammet acidity function (H$_0$) | Acid Type |
| --- | --- | --- | --- |
| Montmorillonite K10 | 273[a] | Wet (3.3 to 1.5), Dry (−5.6 to −8.2) | Bronsted, Lewis |
| Sulfated Zirconia | 77 | −12 | Bronsted, Lewis |
| Amberlyst 15 | 40[a] | (−2.2) | Bronsted |
| Nafion | — | (−11 to −13) | Bronsted |

[a]measured by nitrogen desorption.

In the case of both of these systems, it appears that intermediate carbocations were formed based on the facile isomerization of the olefin at elevated temperatures. However, in order for dimerization to take place, the carbocation must have sufficient stability and charge separation to allow for the reaction with the 1,1-disubstituted primary and tri-substituted internal olefin nucleophiles in solution. MMT-K10 has been shown to be an efficient catalyst for the dimerization of 1,1-disubstituted olefins with intermediate carbocations stabilized by arenes and more recently has been shown to be effective in the dimerization of β-pinene. (Harvey, B. G.; Wright, M. E.; Quintana, R. L. *Preprints of Symposia-ACS Div. Fuel Chem.* 2009, 54, 305-306).

In the case β-pinene, MMT-K10 reacts exothermically at room temperature, whereas stronger heterogeneous acids including Nafion are unreactive except under reflux conditions. A potential explanation for this behavior is that MMT-K10 (an aluminosilicate clay) has Lewis acid sites that can interact with and bind the incoming olefin. This may aid in bringing the olefin in close proximity to the catalyst surface where the olefin can be protonated by a Bronsted acid site at the clay surface. In contrast to acyclic alkenes, β-pinene undergoes a ring opening reaction to produce mixtures of primarily camphene and limonene; these molecules are then converted to dimers. For alkenes including 2-ethyl-1-hexene, one can propose a mechanism in which the alkene is coordinated by a Lewis acid center and then is readily isomerized by a nearby acid group. The potential interaction of 2-ethyl-1-hexene with MMT-K10 is shown below.

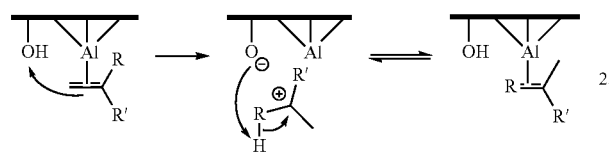

As isomers are formed, they can then recoordinate to a metal center, providing a reversible pathway that may limit the lifetime of carbocations. This premise suggests that even when a highly acidic catalyst including sulfated zirconia is used, the carbocations formed are short-lived and therefore unable to interact with olefins in solution, forming only isomers.

Next, catalysts devoid of Lewis acid sites including Dowex HCR-W2, Amberlyst-15, and Nafion were investigated. Dowex HCR-W2 is a hydrated, gel-type polystyrene-based sulfonic acid resin with no permanent porosity. It was unreactive with the olefin at room temperature and led to slow isomerization at the reflux temperature. Extended periods of reflux led to no observable dimer formation. Amberlyst-15, a low moisture polystyrene-based sulfonic acid resin commonly used for alkylation, dimerization, and oligomerization reactions (Hauge, K.; Bergene, E.; Chen, D.; Fredriksen, G. R.; Holmen, A. Catalysis Today 2005, 100, 463-466; Alcántara, R.; Alcántara, E.; Canoira, L.; Franco, M. J.; Herrera, M.; Navarro, A. *Reactive and Functional Polymers* 2000, 45, 19-27; Cruz, V. J.; Izquierdo, J. F.; Cunill, F.; Tejero, J.; Iberra, M. Fité, C. *Reactive and Functional Polymers* 2005, 65, 149-160), did not react at room temperature, but isomerized and dimerized 2-ethyl-1-hexene at the reflux temperature. Increasing the temperature did not improve the yield of dimer and resulted in some trimer formation.

Nafion, a well studied superacid catalyst that has applications in alkylation and Friedel-Crafts chemistry, olefin isomerization and dimerization reactions (Molnár, Á. *Curr. Org. Chem.* 2008 12, 159-181 Olah, G. A.; Prakash, G. K. S. Molnar, A. Sommer, J. *Superacid Chemistry*, 2nd Edition, Wiley, 2009; Laufer, MC.; Bonrath, W.; Hoelderich, W. F. *Cat. Lett.* 2005, 100, 101-103; Beltrame, P. Zuretti, G. Applied Cat. A-Gen. 2005, 283, 33-38; Wang, H.; Xu, B. Q. Applied Cat. A-Gen. 2004, 275, 247-255; Harmer, M. A.; Sun, Q. *Applied Cat. A-Gen.* 2001, 221, 45-62; Harmer, M. A.; Sun, Q.; Vega, M; Farneth, W E; Heidekun, A.; Hoelderich, W. F. *Green Chem.* 2000, 2, 7-14; Sun, Q.; Harmer, M. A.; Farneth, W. E.; *Chem. Commun.* 1996, 1201-1202; Harmer, M. A.; Sun, Q.; Michalczyk, M. J.; Yang, Z. *Chem. Commun.* 1997, 1803-1804; Harmer, M. A.; Sun, Q. *Adv. Mater.* 1998, 10, 1255-1257; Fujiwara, M.; Shiokawa, K.; Zhu, Y C *J. Mol. Cat. A-Chem.* 2007, 264, 153-161; Harmer, M. A.; Farneth, W. E.; Sun, Q. *J. Am. Chem. Soc.* 1996, 118, 7708-7715; Sun, Q.; Farneth, W. E.; Harmer, M. A. J. Catal. 1996, 164, 62-69; Heidekum, A.; Harmer, M.; Hoelderich, W. F. *Catal. Lett.* 1997, 47, 243-246; Rác, B.; Mulas, G.; Csongrádi, A.; Lóki, K.; Molnár, Á. *Appl. Catal. A.* 2005, 282, 255-265; Fritsch, D.; Randjelovic, I.; Keil, F. *Catal. Today* 2004, 98, 295-308) was unreactive under ambient conditions, but at reflux temperatures, proved to be an excellent catalyst for dimerization and produced a complex array of $C_{16}H_{34}$ molecules in greater than 90% yield (as shown below).

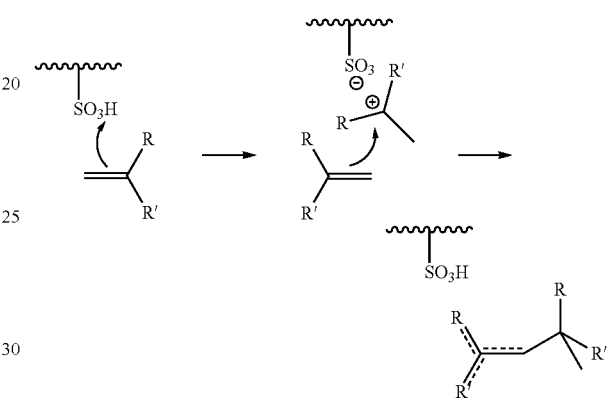

As shown above, a potential dimerization reaction of 2-ethyl-1-hexene on a Nafion or Amberlyst-15 surface Interestingly, neither Amberlyst-15, nor Nafion produced isomers or dimers at ambient temperature, providing further evidence for a mechanism in which Lewis acid sites in the previously discussed inorganic catalysts are important in promoting the isomerization of 2-ethyl-1-hexene at room temperature through initial olefin coordination. As expected, the presence of excess water (wet MMT-K10, Dowex HCR-W2) diminished the capacity of both inorganic and polystyrene supported catalysts to isomerize and dimerize 2-ethyl-1-hexene.

It's important to note that although $H_0$ is often used to describe the acidity of solid acid catalysts, a simple comparison of this value across different catalyst types and in different environments with different substrates is ineffective for the prediction of behavior. In the current study, dry Montmorillonite-K10, with $H_0$ as low as −8.2, efficiently promotes the room temperature isomerization of 2-ethyl-1-hexene, but is completely inactive for the dimerization of the olefin. In a similar manner, sulfated zirconia, which has been characterized as having a Hammet acidity of ~12 is also ineffective for dimerization. In contrast, Amberlyst-15 with a much less acidic $H_0$ (−2.2) was effective at both isomerization and dimerization, while Nafion ($H_0$=−11 to −13) was exceptionally active, particularly when considering the extremely low surface area of the native resin (0.02 m2/g). The results suggest that both Lewis and Bronsted acid sites promote the isomerization of 2-ethyl-1-hexene, but that Lewis acid sites have an inhibitory effect for the dimerization reaction.

Figure 10:
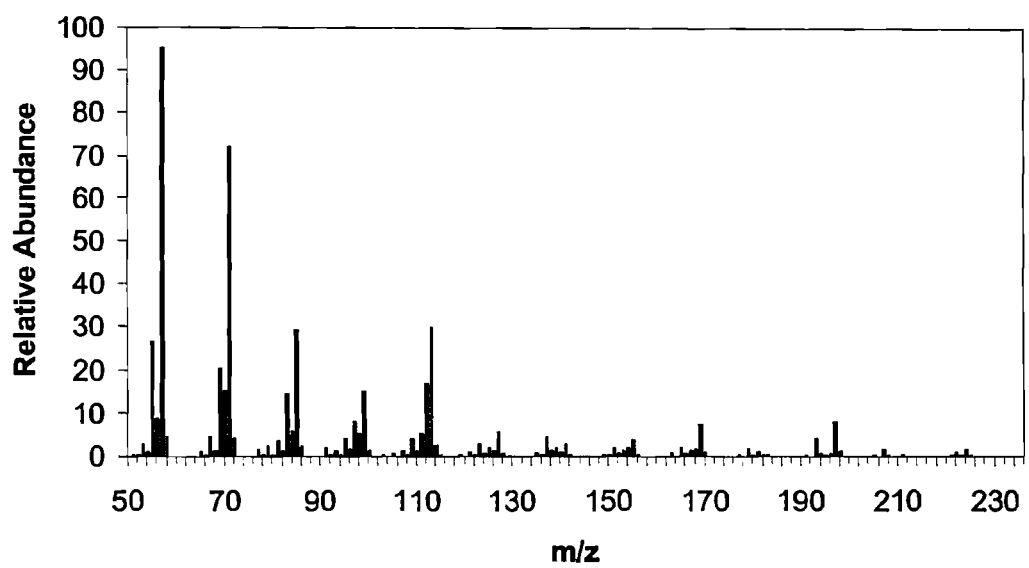
FIG. 10 is a mass spectrum of a typical hydrogenated 2-ethyl-1-hexene dimer, according to embodiments of the invention.

The crude product was separated from the catalysts by simple decantation and analyzed by both GC/MS and NMR spectroscopy. A GC/MS chromatogram (FIG. 9) revealed a complex distribution of compounds that eluted over the course of ca. 2 min on the GC column. A parent ion with m/z 224 was observed for these peaks. This crude mixture was then upgraded through hydrogenation under mild conditions (1-2 psig $H_2$, $PtO_2$ cat.) and subsequent distillation afforded a colorless product. The GC-MS chromatogram was similar to that for the unsaturated solution with the exception that a low intensity parent ion peak with m/z 226 could be detected for some of the compounds. The parent ion peak was unobservable for many of the peaks in the chromatogram, but the saturation of the products and a molecular mass of 226 could be inferred from the splitting pattern (FIG. 10). The saturation of the products was further confirmed through NMR spectroscopy.

An attempt was made to identify individual components of the hydrogenated mixture, but was largely unsuccessful. Based on the structure of 2-ethyl-1-hexene and its subsequent isomers, some inferences can be made in regard to the structures of the products. Potential hydrogenated structures of 2-ethyl-1-hexene dimers (shown below).

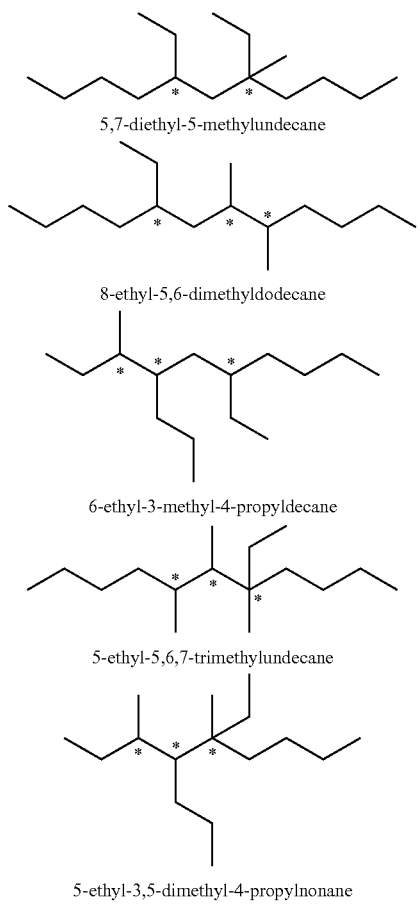

5,7-diethyl-5-methylundecane 8-ethyl-5,6-dimethyldodecane 6-ethyl-3-methyl-4-propyldecane 5-ethyl-5,6,7-trimethylundecane 5-ethyl-3,5-dimethyl-4-propylnonane The proposed product structures each include at least two stereocenters, resulting in a total of 18 GC resolvable isomers, not including more complicated alternative mechanisms including cracking, rearrangements, methyl shifts, and cyclization. Based on the GC chromatograms, the product distribution is very complex; however, the presence of a variety of isomers in solution is beneficial for a potential fuel mixture as it often prevents crystallization and improves the low temperature fluidity of the fuel. Evidence for this effect is provided by the observation that the mixture did not freeze even after being submerged in a −78° C. bath for 2 hours. In addition to having an exceptionally low freezing point, the density of the $C_{16}H_{34}$ mixture was 0.78 g/mL. These physical properties should allow for the use of these mixtures in diesel and high flashpoint jet fuels.

An efficient process for the conversion of 2-ethyl-1-hexene to a complex mixture of $C_{16}H_{34}$ hydrocarbons has been developed. This process allows for the conversion of 1-butene to jet fuel range hydrocarbons in greater than 90% yield. Inorganic catalysts such as sulfated zirconia and MMT-K10 efficiently isomerize 2-ethyl-1-hexene, but do not promote dimerization. Dry cationic exchange resins including Nafion and Amberlyst-15 produce primarily dimers and small amounts of trimers. The results with native Nafion suggest that Nafion nanocomposites would be ideal catalysts for the dimerization reaction. The difference in reactivity between the inorganic catalysts and the cation exchange resins is attributed to interactions between alkenes and Lewis acid centers that inhibit the dimerization reaction. Further work to determine key fuel properties for hydrocarbon mixtures composed exclusively of 2-ethyl-1-hexene dimers as well as mixed systems with hydrogenated butene oligomer mixtures is also being examined.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Embodiments of the invention clearly have military and commercial applications including oil and biofuel companies which may invest in butanol fermentation, refiners, as well as companies that produce polyolefins for polymer applications.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for making diesel/jet fuels, comprising:
   providing an effective amount of 2-ethyl-1-hexene;
   adding active heterogeneous acid catalyst(s) to said 2-ethyl-1-hexene to produce a solvent free mixture;
   heating said solvent-free mixture to greater than about 100° C. at atmospheric pressure or above for a desired amount of time depending on various conditions to selectively produce a $C_{16}$ dimers/catalyst mixture;
   removing said catalyst(s) from said dimers/catalyst mixture; and
   adding hydrogenation catalyst(s) and hydrogenating said dimers under a hydrogen atmosphere to produce a mixture of stable diesel/jet fuels.

2. The process according to claim 1, wherein said step of providing 2-ethyl-1-hexene further comprises a mixture of branched olefins.

3. The process according to claim 2, wherein said catalyst further includes a co-catalyst.

4. The process according to claim 1, wherein said step of adding active heterogeneous acid catalyst(s) to said 2-ethyl-1-hexene is performed under a $N_2$ atmosphere, 5. The process according to claim 1, further comprising the step of purifying said stable fuels by removing 3-methylheptane remaining in said stable diesel/jet fuels.

6. The process according to claim 5, wherein said purifying step includes filtration and/or distillation.

7. The process according to claim 1, wherein said heating step is performed under the temperatures ranging from about 110° C. to about 120° C.

8. The process according to claim 1, wherein said catalyst includes a Ziegler-Natta catalyst.

9. A process for making diesel/fuels, comprising:
providing an effective amount of branched olefins including 2-ethyl-1-hexene;
adding active heterogeneous acid catalyst(s) to said branched olefins to produce a solvent-free mixture;
heating said solvent-free mixture to greater than about 100° C. at atmospheric pressure for a desired amount of time depending on various conditions to selectively produce a $C_{16}$ dimers/catalyst mixture;
removing said catalyst(s) from said dimers/catalyst mixture; and
adding hydrogenation catalyst(s) and hydrogenating said dimers under a hydrogen atmosphere to produce a mixture of stable diesel/jet fuels.

10. The process according to claim 9, wherein said catalyst(s) are selected from the group consisting of supported or unsupported cation exchange resins, acid clays, zeolites, polyoxometallates, sulfated metal oxides, other heterogeneous acids.

11. The process according to claim 9, wherein said fuels are selected from the group consisting of 5,7-diethyl-5-methylundecane, 8-ethyl5,6-dimethyldodecane, 6-ethyl-3-methyl-4-propyldecane, 5-ethyl-5,6,7-trimethylundecane, and 5-ethyl-3,5-dimethyl-4-propylnonane and similar molecules, or molecules produced from the coupling of any two structural isomers of 2-ethyl-1-hexene.

* * * * *